US010620593B2

(12) United States Patent
Kim et al.

(10) Patent No.: US 10,620,593 B2
(45) Date of Patent: Apr. 14, 2020

(54) ELECTRONIC DEVICE AND CONTROL METHOD THEREOF

(71) Applicant: Samsung Electronics Co., Ltd., Suwon-si (KR)

(72) Inventors: Mi-young Kim, Suwon-Si (KR); Tae-ho Hwang, Seongnam-Si (KR); Jin-sung Kim, Seoul (KR); Min-su Hwangbo, Suwon-si (KR); Sun-ah Kim, Seongnam-si (KR); Jong-tae Kim, Suwon-si (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 299 days.

(21) Appl. No.: 15/095,967

(22) Filed: Apr. 11, 2016

(65) Prior Publication Data

US 2016/0363914 A1 Dec. 15, 2016

(30) Foreign Application Priority Data

Jun. 12, 2015 (KR) .................. 10-2015-0083697

(51) Int. Cl.
*G05B 13/02* (2006.01)
*G04G 21/02* (2010.01)
(Continued)

(52) U.S. Cl.
CPC ......... *G05B 13/028* (2013.01); *G04G 21/025* (2013.01); *G06F 1/163* (2013.01);
(Continued)

(58) Field of Classification Search
None
See application file for complete search history.

(56) References Cited

U.S. PATENT DOCUMENTS 5,527,239 A * 6/1996 Abbondanza .......... A63B 22/02
482/1
8,473,043 B1 6/2013 Modarres
(Continued)

FOREIGN PATENT DOCUMENTS

JP 2007-267966 A 10/2007
WO 2014/204092 A1 12/2014

OTHER PUBLICATIONS

Int'l Search Report for PCT/KR2016/006182 dated Aug. 24, 2016 (3 pages).
(Continued)

*Primary Examiner* — Thomas C Lee
*Assistant Examiner* — Gary Collins
(74) *Attorney, Agent, or Firm* — Nixon & Vanderhye P.C.

(57) ABSTRACT

An electronic device is provided comprising a sensor configured to acquire at least one biological signal of a user; a communicator configured to communicate with the external electronic device; and a controller configured to determine a behavior evaluation level of the user based on the at least one biological signal, pairing with the external electronic device, determine control information corresponding to the behavior evaluation level determined and the paired external electronic device, and control the communicator to transmit the determined control information to the paired external electronic device. Accordingly, the electronic device naturally measures the user's behavior patterns and provides a notification to the user, and improves the user's behavior by interworking with an external electronic device.

20 Claims, 23 Drawing Sheets

(51) Int. Cl.
  *G06F 3/01* (2006.01)
  *G06F 1/16* (2006.01)
(52) U.S. Cl.
  CPC .............. *G06F 3/015* (2013.01); *G06F 3/016* (2013.01); *A61B 2562/0219* (2013.01)

(56) References Cited

U.S. PATENT DOCUMENTS

| | | | | |
|---|---|---|---|---|
| 8,814,671 B2* | 8/2014 | Bhogal | .................. | G08B 21/02 463/29 |
| 2002/0120208 A1 | 8/2002 | Kim et al. | | |
| 2005/0124463 A1* | 6/2005 | Yeo | .................... | A61B 5/02427 482/8 |
| 2007/0139553 A1* | 6/2007 | Kister | .................... | G08B 25/14 348/468 |
| 2009/0326406 A1 | 12/2009 | Tan et al. | | |
| 2010/0298649 A1 | 11/2010 | Warkentin et al. | | |
| 2011/0137137 A1 | 6/2011 | hin et al. | | |
| 2012/0229270 A1* | 9/2012 | Morley | .............. | A61B 5/02416 340/539.12 |
| 2012/0315016 A1* | 12/2012 | Fung | .................... | H04N 5/2252 386/248 |
| 2013/0086056 A1 | 4/2013 | Dyor et al. | | |
| 2013/0090065 A1 | 4/2013 | Fisunenko et al. | | |
| 2014/0272847 A1* | 9/2014 | Grimes | .................. | G09B 19/00 434/236 |
| 2014/0276130 A1* | 9/2014 | Mirelman | .............. | A61B 5/744 600/483 |
| 2014/0282270 A1* | 9/2014 | Slonneger | .............. | G06F 3/017 715/863 |
| 2014/0347265 A1* | 11/2014 | Aimone | .................. | G09G 3/003 345/156 |
| 2015/0007307 A1* | 1/2015 | Grimes | .................... | G09B 5/08 726/18 |
| 2015/0145676 A1* | 5/2015 | Adhikari | ................ | A61B 5/1112 340/539.32 |
| 2015/0297109 A1* | 10/2015 | Garten | ................ | A61B 5/04845 600/544 |
| 2015/0338917 A1* | 11/2015 | Steiner | .................. | H04L 9/3231 345/156 |
| 2015/0351655 A1* | 12/2015 | Coleman | .............. | A61B 5/0482 600/301 |
| 2016/0014307 A1 | 1/2016 | Peng et al. | | |
| 2016/0077547 A1* | 3/2016 | Aimone | .................. | G06F 3/012 345/8 |
| 2016/0143079 A1 | 5/2016 | Yoon et al. | | |
| 2017/0339484 A1* | 11/2017 | Kim | .................... | H04R 1/1041 |

OTHER PUBLICATIONS

Written Opinion for PCT/KR2016/006182 dated Aug. 24, 2016 (8 pages).

* cited by examiner

|  | Measurement Items | Collection Units | Measurements |
|---|---|---|---|
| Activity | Heart Rate | Times/Minute | PPG Sensor |
|  | Breathing Rate | Times/Minute | PPG Sensor |
|  | Moving Distance | Km/Hour | 3-Axis Acceleration Sensor |
|  | Number of Steps | Times/Hour | 3-Axis Acceleration Sensor |
|  | Holding Time of Each Type of Motion (running, walking, sitting) | Time/Day | 3-Axis Acceleration Sensor, GPS |
|  | Number of Times of Finger Movements | Times/Minute | EMG Sensor |
| Linguist Behavior | Voice Volume | dB/Hour | Microphone (Voice Analysis) |
|  | Speaking Time | Time/Day |  |
|  | Crying Time | Time/Day |  |
|  | Number of Times of Using Specific Word | Time/Day |  |
|  | Number of Times of Interrupting Talk | Time/Day |  |
| Impulsivity | Holding Time of Emotional State (Excitement, Anger) | Time/Day | Change in Skin Temperature, Heart Rate, GSR, Breathing, EMG, etc. |
|  | Number of Times of Changing Emotional State | Time/Day |  |

310 — Activity
320 — Linguist Behavior
330 — Impulsivity

FIG. 3

| Types of External Devices | CONTROL INFORMATION | | | BEHAVIOR EVALUATION LEVEL | | | | |
|---|---|---|---|---|---|---|---|---|
| | | Type | Applicability | Serious | Bad | Normal | Good | Very Good |
| Smartphone /Tablet (Console) | reward | Allow Login | ○ | | | | | |
| | | Extend Content Type | ○ | | | ○ Provide Training Content Option | ○ Regardless of Device Type (5 hours in total) | ○ Unrestricted |
| | | Increase Usage Time | ○ | | ○ Designated Training Content (Restrict Movement between Contents) | ○ Internet Browser App (20 minutes in total) | | |
| | | Increase Cyber Money | ○ | ○ Provide Only Basic Function (Calling, Texting, etc.) | ○ Internet Brower App (20 minutes in total) | ○ Music App (2 hours in total) | ○ Cyber Money (15,000 won in total) | ○ Cyber Money (20,000 won in total) |
| | | Increase Data Capacity | △ | | | ○ SNS App (20 minutes in total) | | |
| | Punishment | Not Allow Login | ○ | | | | | |
| | | Restrict Content Type | ○ | | ○ Music App (1 hour in total) | ○ One Wish List App (1 hour in total) | | |
| | | Reduce Usage Time | ○ | | | | | |
| | | Reduce Cyber Money | ○ | | | | | |
| | | Reduce Data Capacity | △ | | | | | |
| HMD | reward | Allow Login | ○ | | | | | |
| | | Extend Content Type | ○ | ○ Provide Only Basic Function (Calling, Texting, etc.) | ○ Designated Training Content (Restrict Movement between Contents) | ○ Provide Training Content Option | ○ Regardless of Device Type (5 hours in total) | ○ Unrestricted |
| | | Increase Usage Time | ○ | | | ○ Movie (1 movie in total) | ○ Cyber Money (15,000 won in total) | ○ Cyber Money (20,000 won in total) |
| | Punishment | Not Allow Login | ○ | | | | | |
| | | Restrict Content Type | ○ | | | | | |
| | | Reduce Usage Time | ○ | | | | | |
| PC /Laptop | reward | Allow Login | ○ | | | ○ Designated Training Content (Restrict Movement between Contents) | ○ Designated Training Content (Restrict Movement between Contents) | ○ Unrestricted |
| | | Extend Content Type | ○ | ○ Designated Training Content (Restrict Movement between Contents) | ○ Designated Training Content (Restrict Movement between Contents) | ○ Internet Brower (2 hours in total) | ○ Internet Brower (3 hours in total) | ○ Cyber Money (20,000 won in total) |
| | | Increase Usage Time | ○ | ○ Internet Brower (1 hour in total) | ○ Internet Brower (2 hours in total) | ○ SNS (40 minutes in total) | ○ SNS (1 hour in total) | |
| | | Not Allow Login | ○ | | ○ SNS (20 minutes in total) | ○ One Designated App (30 minutes in total) | ○ Two Designated Apps (1 hour in total) | |
| | Punishment | Restrict Content Type | ○ | | | | | |
| | | Reduce Usage Time | | ○ | | | ○ Cyber Money (15,000 won in total) | |
| TV | reward | Allow Login | ○ | | | | | |
| | | Extend Content Type | ○ | ○ Designated Training Content and Channel (Restrict Channel Change) | ○ Provide Training Content Option | ○ Provide Training Content Option | ○ Provide Training Content Option | ○ Unrestricted |
| | | Increase Usage Time | ○ | | ○ Education Broadcast (3 hours in total) | ○ Education Broadcast (3 hours in total) | ○ Education Broadcast (3 hours in total) | ○ Cyber Money (20,000 won in total) |
| | | Not Allow Login | ○ | | | ○ Designated Channel (1 hours in total) | ○ Two Designated Channels (2 hours in total) | |
| | Punishment | Restrict Content Type | ○ | | | | ○ Cyber Money (15,000 won in total) | |
| | | Reduce Usage Time | ○ | | | | | |

FIG. 11

ELECTRONIC DEVICE AND CONTROL METHOD THEREOF

RELATED APPLICATION(S)

This application claims priority from Korean Patent Application No. 10-2015-0083697, filed on Jun. 12, 2015, in the Korean Intellectual Property Office, the disclosure of which is incorporated herein by reference in its entirety.

BACKGROUND

Apparatuses and methods consistent with exemplary embodiments relate to an electronic device and a control method thereof, and more particularly, to an electronic device which measures a user's behavior pattern and provides feedback, and a control method thereof.

Thanks to the development of electronic technologies, various kinds of electronic products are developing and are being distributed. In particular, various kinds of display devices such as a television (TV), a mobile phone, a Personal Computer (PC), a laptop PC, a Personal Digital Assistant (PDA), and the like, are mostly used in general households. In addition, electronic devices which can be worn like glasses, watch, clothing, and the like, and can be always worn without causing inconvenience to users, like a part of the human body. In particular, wearable devices are being distributed.

Accordingly, functions performed by the electronic device become diversified. In particular, the electronic device may collect biometric information, behavior reaction information, and the like, since the electronic device can be worn on the user's body, and perform various functions based on the collected information.

In this regard, there is a need for a method for improving user's behavior by collecting and measuring user's normal behavior patterns and providing appropriate feedback based on the collected and measured user's behavior patterns. In addition, there is a need for the electronic device to provide feedback to the user by interworking with a server.

Therefore, the present disclosure provides various methods for measuring user's behavior patterns and providing feedback to improve user's behavior.

SUMMARY

Exemplary embodiments of the present disclosure overcome the above disadvantages and other disadvantages not described above. Also, the present disclosure is not required to overcome the disadvantages described above, and an exemplary embodiment of the present disclosure may not overcome any of the problems described above.

The present disclosure provides an electronic device which transmits, to an external electronic device, control information for controlling the external electronic device to operate in a pre-set environment according to a determined user's behavior evaluation level, and a control method thereof.

According to an aspect of the present disclosure, a control method of an electronic device which controls an external electronic device includes: acquiring at least one biological signal of a user; determining a behavior evaluation level of the user based on the at least one biological signal; pairing with the external electronic device; determining control information corresponding to the behavior evaluation level determined and the paired external electronic device; and transmitting the control information determined to the paired external electronic device.

The control information may include at least one of available time information, available content information, and a control command regarding the paired external electronic device.

The behavior evaluation level may be determined based on a value which is calculated by digitizing the at least one biological signal acquired by weighting at least one item of activity, linguistic behavior, and impulsivity.

The available time information, the available content information, and the control command may be variable according to the determined behavior evaluation level.

The transmitting may include, in response to the user of the electronic device performing user authentication with respect to the paired external electronic device, transmitting the control information to the external electronic device.

The control method may further include providing feedback according to the determined behavior evaluation level.

The control method may further include receiving an input of user manipulation to set a behavior improvement item of the user and a behavior pattern measuring time, and the acquiring the at least one biological signal may include determining a behavior pattern related to the set item, and detecting data for measuring the determined behavior pattern according to the set time.

The determining the behavior evaluation level may include: grouping user's behavior patterns which are measured based on the at least one biological signal to predetermined items; calculating an average by weighting the grouped user's behavior patterns according to each of the items, and determining the behavior evaluation level based on the calculated average.

The determining the behavior evaluation level may include comparing the calculated average and a predetermined reference value and determining the behavior evaluation level according to a deviation.

The control method may further include storing behavior pattern history information of the user, and the determining the behavior evaluation level may include measuring a similarity between a behavior pattern of the user which is measured based on the at least one biological signal, and the behavior pattern history information of the user, and determining the behavior evaluation level.

The control method may further include transmitting, to the paired external electronic device, a control signal for displaying an image on the user through the paired external electronic device according to the determined behavior evaluation level.

According to another aspect of the present disclosure, an electronic device which controls an external electronic device includes: a sensor configured to acquire at least one biological signal of a user; a communicator configured to communicate with the external electronic device; and a controller configured to determine a behavior evaluation level of the user based on the at least one biological signal, pair with the external electronic device, determine control information corresponding to the behavior evaluation level determined and the paired external electronic device, and control the communicator to transmit the control information determined to the paired external electronic device.

The control information may include at least one of available time information, available content information, and a control command regarding the paired external electronic device.

The control command may include information for controlling the paired external electronic device to operate based on at least one of the available time information and the available content information.

The behavior evaluation level may be determined based on a value which is calculated by digitizing the at least one biological signal acquired by weighting at least one item of activity, linguistic behavior, and impulsivity.

The available time information, the available content information, and the control command may be variable according to the determined behavior evaluation level.

In response to the user of the electronic device performing user authentication with respect to the paired external electronic device, the controller may be configured to transmit the control information to the external electronic device.

The controller may be configured to provide feedback according to the determined behavior evaluation level.

The electronic device may further include an input configured to receive an input of user manipulation to set a behavior improvement item of the user and a behavior pattern measuring time, and the controller may be configured to determine a behavior pattern related to the set item, and control the sensor to detect data for measuring the determined behavior pattern according to the set time.

According to another aspect of the present disclosure, a system includes: a communicator configured to communicate with a first electronic device and a second electronic device; and a controller configured to determine a behavior evaluation level of a user based on at least one biological signal received from the first electronic device, in response to information on the second electronic device paired with the first electronic device being received from at least one of the first electronic device and the second electronic device, determine control information corresponding to the behavior evaluation level and the information on the second electronic device, and transmit the determined control information to the second electronic device.

According to various exemplary embodiments as described above, the electronic device naturally measures the user's behavior patterns and provides a notification to the user, and improves the user's behavior by interworking with an external electronic device.

Additional and/or other aspects and advantages of the disclosure will be set forth in part in the description which follows and, in part, will be obvious from the description, or may be learned by practice of the disclosure.

BRIEF DESCRIPTION OF THE DRAWINGS

The above and/or other aspects of the present disclosure will be more apparent by describing certain exemplary embodiments of the present disclosure with reference to the accompanying drawings, in which:

FIG. 3 is a view showing data for measuring a user's behavior pattern, that is, examples of biological signals, according to an exemplary embodiment;

FIG. 11 is a view showing various examples of usage environments included in control information according to an exemplary embodiment;

DETAILED DESCRIPTION

Hereinafter, exemplary embodiments will be described in greater detail with reference to the accompanying drawings. In the following description, well-known functions or constructions are not described in detail since they would obscure the disclosure in unnecessary detail. Also, the terms used herein are defined according to the functions of the present disclosure. Thus, the terms may vary depending on a user's or an operator's intention and usage. That is, the terms used herein must be understood based on the descriptions made herein.

Figure 1:
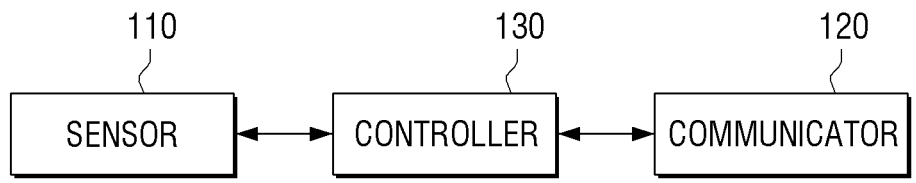
FIG. 1 is a block diagram showing a configuration of an electronic device according to an exemplary embodiment.

FIG. 1 is a block diagram showing a configuration of an electronic device 100 according to an exemplary embodiment.

Referring to FIG. 1, the electronic device 100 includes a sensor 110, a communicator 120, and a controller 130. The electronic device 100 used in the present specification refers to an electronic device which acquires a plurality of biological signals of a user, and determines a behavior evaluation level of the user from among normal electronic devices. The electronic device 100 may be implemented by using, but not limited to, a TV, a laptop, a tablet, a desktop, a set-top box, a game console, a stereo, a mobile phone, a smart watch, an earphone, glasses, goggles, a helmet, a hair band, a Head Mounted Display (HMD), a bracelet, a ring, a necklace, shoes, clothing, a hat, a shoe sticker, a clip, and the like.

In particular, the electronic device 100 according to an exemplary embodiment may include a wearable device which is used by interworking with a smartphone or a tablet wirelessly. In the following description, the electronic device 100 is implemented by using a smart watch from among the above-described kinds of devices by way of an example, and it should be understood that the operations of the electronic device 100, which will be described below, can be applied to the above-described kinds of devices.

The electronic device 100 according to an exemplary embodiment aims at controlling a range of use of an external electronic device (not shown). The electronic device 100 may control the range of use of the external electronic device through wire/wireless communication methods.

In addition, the external electronic device recited herein refers to an electronic device except for an electronic device which acquires user's biological signals and determines a user's behavior evaluation level, and may be implemented by using a TV, a laptop, a tablet, a desktop, a set-top box, a game console, a stereo, a mobile phone, and the like. That is, the external electronic device according to an exemplary embodiment refers not to an electronic device for acquiring user's biological signals and determining a user's behavior evaluation level, but to an electronic device that a user normally uses to reproduce contents.

The range of use of the external electronic device refers to a predetermined condition, a predetermined range, or a predetermined mode in which the external electronic device operates in response to a user's behavior evaluation level when the user of the electronic device 100 uses the external electronic device. That is, as will be described below, the range of use of the external electronic device may be changed according to the behavior evaluation level of the user of the electronic device 100. Specifically, the operating time of the external electronic device or a kind of program executable in the external electronic device may be changed. That is, the range of use of the external electronic device recited in the present specification refers to at least one of a time during which the external electronic device can operate and a service that the external electronic device can provide in response to the user of the electronic device 100.

To distinguish between the electronic device 100 and the external electronic device, the electronic device 100 matches a first electronic device, and the external electronic device matches a second electronic device in the present specification.

The sensor 110 may acquire data including at least one of a user's biological signals and usage information of the first electronic device 100.

The biological signals refer to electrical signals between minute cells of a human body. Exemplary biological signals include, but are limited to, brainwaves, electromyograms (EMG), electrocardiograms (ECG), and the like. The sensor 110 may measure, data indicative of one or more of biological signals, heart rates, breathing rates, moving distances, a number of steps taken, a holding time of each type of motion, a number of times of finger movements, a voice volume, a speaking time, a crying time, the number of times of using a specific word, the number of times of interrupting a talk, a holding time of an emotional state, the number of times of changing an emotional state, and the like.

In addition, the usage information of the first electronic device 100 refers to information which is generated while the user uses the first electronic device 100 directly/indirectly. The usage information generated while the user directly uses the first electronic device 100 may include information on usage history generated while the user directly manipulates the first electronic device 100, the number of times of manipulating the first electronic device 100, the number of times of touching, the number of times of pressing a function key, the number of times of toggling a screen, the number of times of uttering a voice command, the number of times of detecting a motion, and the like. That is, the information generated while the user directly uses the first electronic device 100 includes some or all of the information generated while the user directly manipulates the first electronic device 100.

In addition, the information generated while the user indirectly uses the first electronic device 100 refers to information generated based on behavior that the user exhibits without any intention to use the first electronic device 100. For example, the behavior that the user exhibits, a voice that the user utters, a gaze direction, eye blinking, and the like, when the user puts the first electronic device 100 on a table without wearing the first electronic device 100 may be detected via a camera lens, an infrared sensor, a microphone, and the like, provided on the first electronic device 100. Therefore, the first electronic device 100 may acquire information on the user even when the user does not directly manipulate the first electronic device 100. In the present specification, the information on the user that is acquired when the user does not directly manipulate the first electronic device 100 is defined as the information generated while the user uses the first electronic device 100 indirectly.

Specifically, the sensor 110 includes various sensors to measure or detect a user's normal behavior pattern. For example, the sensor 110 may include a Photo-Plethysmography (PPG) sensor to measure a heart rate or a breathing rate, an acceleration sensor or a gyro sensor to measure a moving distance, a number of steps taken, rotation, and the like, a Galvanic Skin Response (GSR) sensor to measure GSR, a body temperature sensor to measure body temperature, an EMG sensor to measure an EMG, a Global Positioning System (GPS) sensor to acquire location information, an ECG sensor to measure an ECG, a motion sensor to detect a user's motion, and the like, and may include a microphone to receive a user's voice. In addition, the sensor 110 is not limited to the above-mentioned sensors and may include various sensors to measure user's location, motion, biological signals, and the like.

In addition, the controller 130 may measure a user's behavior pattern based on data detected, sensed, or measured through the sensor 110. For example, in response to data regarding a user's heart rate being detected through the PPG sensor, the controller 130 may analyze the data regarding the heart rate and measure a behavior pattern on the heart rate, for example, whether the heart rate is fast, slow, regular, or irregular. The data detected through the sensor 110 will be explained in detail below with reference to FIG. 3.

The communicator 120 of FIG. 1 may communicate with a second electronic device (not shown) according to various kinds of communication methods. The communicator 120 may communicate with the at least one second electronic device through various communication methods such as Bluetooth (BT), Wireless Fidelity (WiFi), Zigbee, Infrared (IR), a serial interface, a Universal Serial Bus (USB), Near Field Communication (NFC), and the like. In addition, the second electronic device may be implemented by using various types of electronic devices such as a TV, an electronic board, an electronic table, a Large Format Display (LFD), a smartphone, a tablet, a desktop PC, a laptop, a server, and the like.

In addition, in response to a user's behavior evaluation level which is determined based on data detected through the sensor 110, the controller 130 may control to transmit, to the second electronic device paired with the first electronic device 100, control information for allowing the second electronic device to operate within a predetermined range of use.

Specifically, the controller 130 may determine the behavior evaluation level of the user based on the user's behavior pattern measured. In addition, the controller 130 may control the communicator 120 to pair with the second electronic device. A pairing may generally mean that a communication session is established between the first electronic device 100 and the second electronic device so as to match the first electronic device 100 and the second electronic device to enable communication therebetween on a network. The pairing may be performed through WiFi, WiFi Direct, Bluetooth, and the like.

In addition, the controller 130 may determine control information corresponding to the behavior evaluation level determined and the paired second electronic device, and transmit the control information determined to the paired second electronic device. Specifically, in response to having paired the first electronic device 100 with the second electronic device, the communicator 120 may receive identification information for identifying the second electronic device from the paired second electronic device. In some embodiments, the identification information may include the type, product number, serial number, device name, and network address (media access control (MAC)/Internet Protocol (IP) address) of the second electronic device. The controller 130 may acquire information on the paired second electronic device such as the type, product number, serial number, device name, network address (MAC/IP address), and the like, of the second electronic device through the identification information of the second electronic device. In addition, in response to the second electronic device having been identified based on the information on the second electronic device, the controller 130 may determine control information corresponding to the identified second electronic device and the determined behavior evaluation level. For example, the controller 130 may identify whether the identified second electronic device is a TV, an HMD device, or a laptop, and determine control information corresponding to the identified type of the second electronic device and the determined behavior evaluation level. Such control information may include information on the type of the second electronic device, an available time, an allowable content, and the like, and a detailed description thereof will be provided below. In addition, the control information may be physically implemented by using a data packet, a transmission frame, and the like.

Hereinafter, a process indicating the overall operations of the controller 130 will be explained with reference to FIG. 2.

Figure 2:
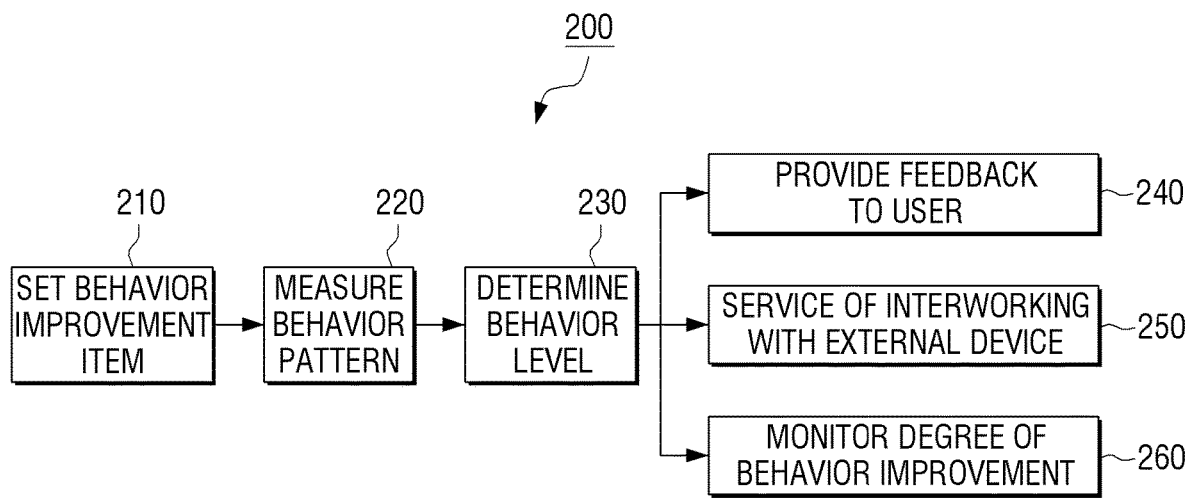
FIG. 2 is a view to illustrate an operation process of a controller according to an exemplary embodiment.

FIG. 2 is a view to illustrate an operation process 200 of a controller (e.g., similar to the controller 130 of FIG. 1) according to an exemplary embodiment.

Referring to FIG. 2, in response to a behavior improvement item having been set at operation 210, the controller 130 measures a user's behavior pattern based on data detected according to the set behavior improvement item at operation 220, and determines a user's behavior evaluation level or behavior level based on the measured behavior pattern at operation 230. In addition, the controller 130 may provide an appropriate behavior improvement service according to the behavior level determined at operation 230. That is, the behavior improvement service may include providing feedback to the user at operation 240, providing a service by interworking with the second electronic device at operation 250, and providing a service of monitoring a degree of behavior improvement at operation 260.

The behavior evaluation level recited herein refers to an evaluation level which corresponds to a user's behavior. The evaluation level of a user may be determined based on a value calculated by digitizing a user's behavior according to a biological signal-related item. Specifically, an evaluation level corresponding to a user's behavior may be selected or determined from among a plurality of predetermined evaluation levels based on an average calculated from data acquired through the sensor 110, and the determined evaluation level corresponds to the user's behavior evaluation level. In particular, such a behavior evaluation level may be determined based on a value which is calculated via digitizing the biological signals and weighting at least one item of activity, linguistic behavior, and impulsivity.

In addition, the control information may include at least one of available time information, available content information, and a control command regarding the second electronic device, and the second electronic device may be operated based on the control information. For example, when the range of use of the second electronic device concerns the operable time of the second electronic device and the service that the second electronic device can provide in response to the user of the first electronic device 100, the control information may include information on how long the second electronic device can operate, information on the type of the service that the second electronic device can provide, and control information for allowing the second electronic device to operate according to the operable time and the type of the service.

In FIG. 2, in response to the behavior improvement item having been set at operation 210, the controller 130 of the first electronic device 100 measures the behavior pattern at operation 220, and determines the behavior evaluation level at operation 230, provides feedback to the user at operation 240, interworks with the external device at operation 250, and monitors the degree of behavior improvement at operation 260. However, the controller 130 may process the above-described operations by interworking with a server (not shown), and a detailed description thereof will be provided below.

That is, the controller 130 may measure the user's behavior pattern from the data detected through the sensor 110, determines the user's behavior evaluation level from the measured behavior pattern, and then provides an appropriate behavior improvement service according to the user's behavior evaluation level, and hereinafter, these operations will be explained in detail.

FIG. 3 is a view showing data for measuring a user's behavior pattern, that is, examples of biological signals, according to an exemplary embodiment.

Referring to FIG. 3, the biological signals for measuring the user's behavior pattern may be largely divided into an activity item 310, a linguistic behavior item 320, and an impulsivity item 330. The activity item 310 may include information on a heart rate, a breathing rate, a moving distance, a number of steps, a holding time of each type of motion (running, walking, or sitting), the number of times of finger movements, and the like. The linguistic behavior item 320 may include information on a voice volume, a speaking time, a crying time, a number of times of using a specific word, and a number of times of interrupting a talk. The impulsivity item 330 may include information on a holding time of an emotional state (excitement or anger), a number of times of changing an emotional state, and the like. Data for measuring the user's behavior pattern is not limited to the examples shown in FIG. 3, and may include a number of times of repeating wearing/taking off of an electronic device (e.g., the electronic device 100 of FIG. 1) during use of the electronic device, a menu movement interval time, an ability to perform a given task, a brainwave, and the like, and, in addition, may include some or all information on the user's biological signals, voice, motion, emotional change, movement, and the like.

The sensor 110 (of FIG. 1) may detect the data for measuring the user's behavior pattern in a predetermined period. For example, the PPG sensor included in the sensor 110 may detect the user's heart rate, that is, how many times user's heart beats per minute, and also, detect the user's breathing rate, that is, how many times the user breathes per minute. The acceleration sensor included in the sensor 110 may detect how many kilometers the user moves in one hour and detect the number of steps per hour, and may detect how many hours a day the user holds each type of motion such as running, walking, or sitting. In addition, the microphone included in the sensor 110 may detect at what decibel level the user's voice volume is on average per day and how many hours a day the user speaks. In addition, the microphone included in the sensor 110 may detect how many hours a day the user cries, how many times a day the user uses a specific word, and how many times a day the user interrupt a talk.

In addition, the GSR sensor included in the sensor 110 may detect how many hours a day the user's emotional state (excitement or anger) is held and how many times a day the user's emotional state is changed In addition, the touch sensor included in the sensor 110 may detect how many times a day the user repeats wearing/taking off of the electronic device, and how many times a menu moves per minute.

In addition, the period in which the sensor 110 detects the data for measuring the user's behavior pattern may be changed according to user's manipulation. In addition, the controller 130 may calculate an average of values detected through the sensor 110 in the predetermined period. For example, the controller 130 may calculate an average voice volume of the user for one day based on the user's voice volumes detected through the microphone included in the sensor 110 for one day. In addition, the average calculated in the predetermined period may be used as a sensing representative value.

In addition, the controller 130 may measure a behavior pattern from the data detected through the sensor 110. For example, in response to the user's heart rate having been detected as 70 times per minute through the sensor 110, the controller 130 may use the heart rate in evaluating the user's behavior based on information on a previous heart rate and information on the current heart rate. The behavior pattern regarding the heart rate may indicate whether the heart rate becomes faster, becomes slower, is irregular, and regular.

In another example, in response to the number of times of changing the emotional state having been detected as 2 for one day through the sensor 110, the controller 130 may measure a behavior pattern regarding the number of times of changing the emotional state based on information on the number of times of changing the emotional state previously detected and information on the number of times of changing the emotional state currently detected. The behavior pattern regarding the number of times of changing the emotional state may indicate whether the user is emotionally unstable or stable.

In another example, in response to a brainwave having been detected through the sensor 110, the controller 130 may measure a behavior pattern regarding the brainwave based on information on a previous brainwave and information on the current brainwave. Specifically, the controller 130 may measure the behavior pattern regarding the brainwave based on how the frequency of the brainwave is and how the shape of the brainwave is changed.

In addition, the sensor 110 may detect data corresponding to a user's behavior improvement item according to a behavior pattern measuring time. This will be explained in detail below with reference to FIG. 4.

Figure 4:
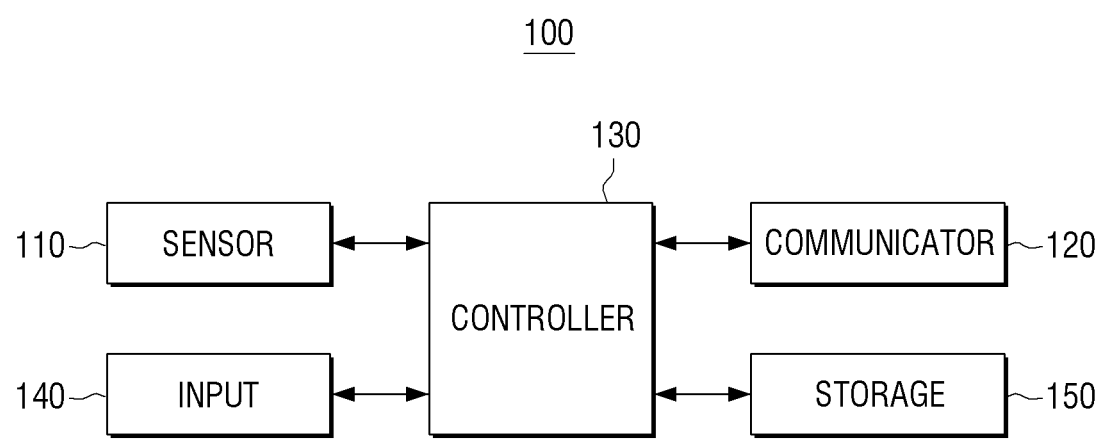
FIG. 4 is a block diagram showing a configuration of an electronic device according to another exemplary embodiment.

FIG. 4 is a block diagram showing a configuration of a first electronic device 100 according to another exemplary embodiment.

Referring to FIG. 4, the first electronic device 100 includes a sensor 110, a communicator 120, a controller 130, an input 140, and a storage 150. The sensor 110, the communicator 120, and the controller 130 are the same as described above and thus a detailed description thereof is omitted.

The first electronic device 100 may further include the input 140. The input 140 recited herein may receive an input of user manipulation to set a user's behavior improvement item and a behavior pattern measuring time.

The input 140 may be implemented by using a display provided with a touch panel, a physical function key, and the like, and the user may input a behavior improvement item of a behavior that the user wishes to improve, and a behavior pattern measuring time through the input 140. In addition, the behavior improvement item and the behavior pattern measuring time may be displayed on the display in the form of a Graphic User Interface (GUI) of a user interface screen, an icon, or the like.

For example, the behavior improvement item may include an item of attention and concentration during classes/study hours, an item of sleepiness during classes/study hours, an item of hyperactivity in a seat during classes/study hours, an item of use of specific slang/swear word, an item of crying loudly or shouting, and the like.

In addition, the behavior pattern measuring time may include a school hour item, an independent study time item, and the like. In addition, the behavior pattern measuring time may include an item for setting a specific time range such as from 9 am to 3 pm. The behavior pattern measuring time may be selected automatically or manually based on a schedule stored in a mobile device or a server.

Accordingly, the user may set a desired behavior improvement item and set a desired behavior pattern measuring time.

In addition, the controller 130 may determine a behavior pattern related to the set behavior improvement item. For example, when the set behavior improvement item is the item of attention and concentration during classes/study hours, the controller 130 may determine a necessary behavior pattern in relation to the item of attention and concentration during classes/study hours, such as a holding time of each type of motion (sitting), the number of times of finger movements, a speaking time, the number of times of using a specific word, and the like.

In addition, the controller 130 may control the sensor 110 to detect data for measuring the determined behavior pattern according to the set behavior pattern measuring time. That is, regarding the item of attention and concentration during classes/study hours, the controller 130 may control the sensor 110 to detect the data for measuring the necessary behavior pattern, such as the holding time of each type of motion (sitting), the number of times of finger movements, the speaking time, the number of times of using a specific word, during school hours.

In addition, the controller 130 may detect whether the user wears the first electronic device 100 or not through the sensor 110, and, only when the user wears the first electronic device 100, the controller 130 may activate the sensor 110 and control the sensor 110 to detect the data for measuring the user's behavior pattern automatically. The controller 130 may control the sensor 110 to detect a behavior pattern which can be detected even when the user does not wear the first electronic device 100, such as a user's motion, dilation of pupils, gaze, and the like.

In addition, as described above, the controller 130 may control the sensor 110 to detect the data for measuring the user's behavior pattern based on the behavior pattern measuring time set according to user manipulation through the sensor 110, and the other time.

The controller 130 may determine whether the user sleeps or not based on the user's brainwave, heart rate, breathing rate, and the like, detected through the sensor 110, and, when it is determined that the user sleeps, the controller 130 may control the sensor 110 not to detect the data for measuring the user's behavior pattern. In addition, when it is determined that the user sleeps, the controller 130 may not consider the detected data for measuring the user's behavior pattern in determining a user's behavior evaluation level afterward.

In addition, the controller 130 may determine whether the user is in an indoor space or an outdoor space based on data detected through a light intensity sensor, the GPS sensor, the acceleration sensor, and the like, of the sensor 110, and, only when the user is in the indoor space, the controller 130 may control the sensor 110 to detect the data for measuring the user's behavior pattern. The controller 130 may determine whether the user is in the indoor space or the outdoor space by analyzing a background noise or using a GPS receiving rate, a WiFi receiving rate, or motion recognition within a radius of a specific range.

Figure 5:
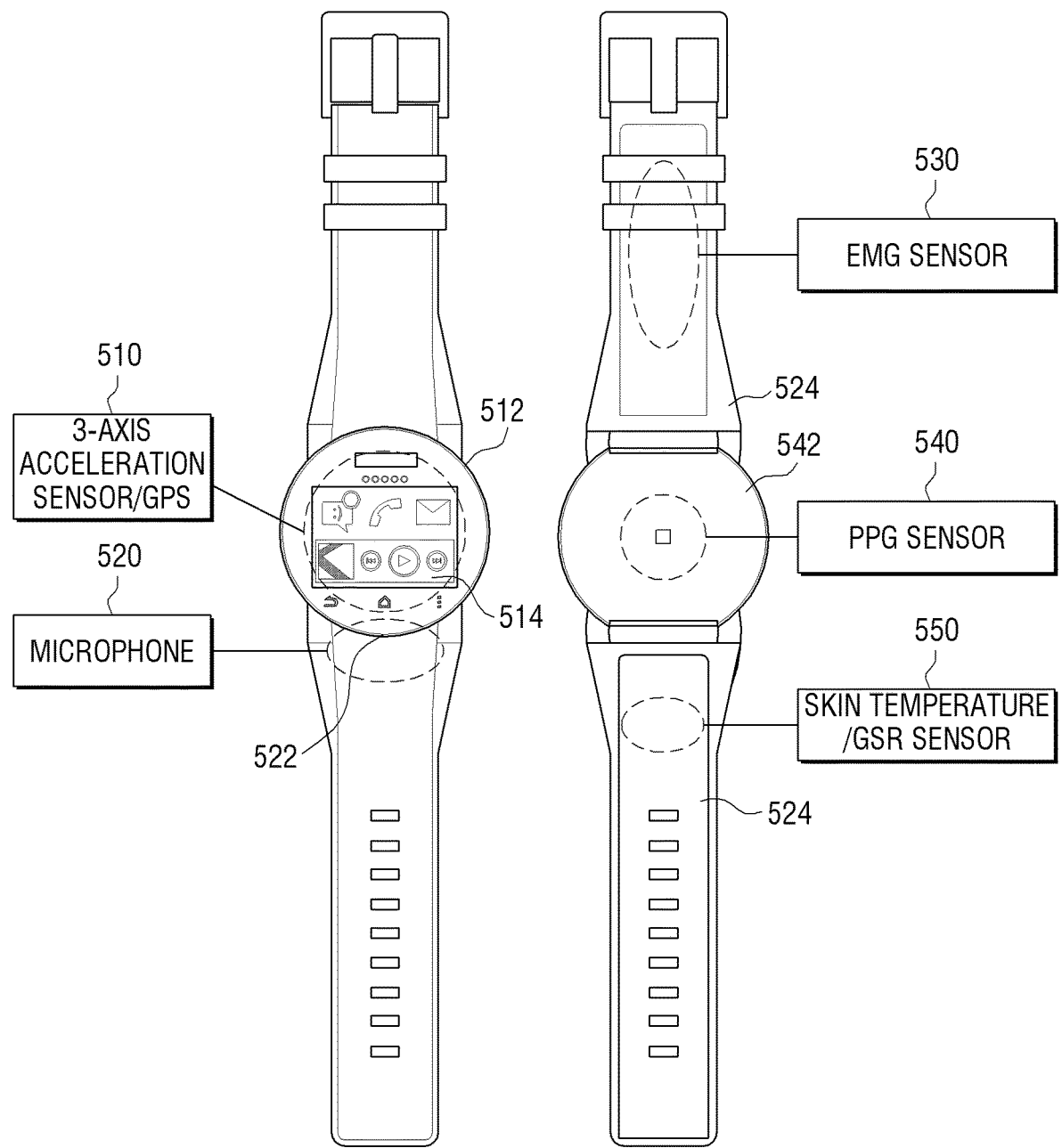
FIG. 5 is a view showing an electronic device including various sensors according to an exemplary embodiment.

FIG. 5 is a view showing a first electronic device 100 including various sensors according to an exemplary embodiment.

Referring to FIG. 5, the first electronic device 100 is in form of a smart watch. A three-axis acceleration sensor or a GPS sensor 510 may be provided inside a front surface 512 of a display 514 of the smart watch, a microphone 520 may be provided on a side 522 of the display 514 of the smart watch, and an EMG sensor 530 and a skin temperature/GSR sensor 550 may be provided on a band 524 of the smart watch. In addition, a PPG sensor 540 may be provided inside a rear surface 542 of the display 514 of the smart watch. The arrangements of the various sensors in FIG. 5 are merely an example and the sensors may be arranged on various locations in the smart watch and the band.

The controller 130 may determine a user's behavior evaluation level based on the user's behavior pattern measured based on the detected data.

Specifically, the controller 130 may group the measured user's behavior patterns to predetermined items, calculate an average by weighting the grouped user's behavior patterns according to each of the items, and determine the behavior evaluation level based on the calculated average.

Referring to FIG. 3, the heart rate, the breathing rate, the moving distance, the number of steps, and the holding time of each type of motion may be grouped to the activity item 310 of FIG. 3, the voice volume, the speaking time, the crying time, the number of times of using a specific word, the number of times of interrupting a talk may be grouped to the linguistic behavior item 320 of FIG. 3, and the holding time of the emotional state (excitements or anger) and the number of times of changing the emotional state may be grouped to the impulsivity item 330 of FIG. 3.

In addition, although not shown in FIG. 3, the number of times of repeating wearing/taking off of the electronic device and a menu movement interval time may be grouped to a device manipulation pattern item, an achievement ability during a training, such as neurofeedback, cognitive training, may be grouped to a training achievement ability item, and a brainwave measured using an HMD, and a brainwave, a change in a beta/theta wave, and a change in a concentration brain wave indicator, which are measured in a daily life or during a training using a device, may be grouped to a brainwave change item.

The grouping items and the above-described example in FIG. 3 are merely examples, and the voice volume, the crying time, and the like, may be redundantly grouped to the impulsivity item 330.

Figure 6:
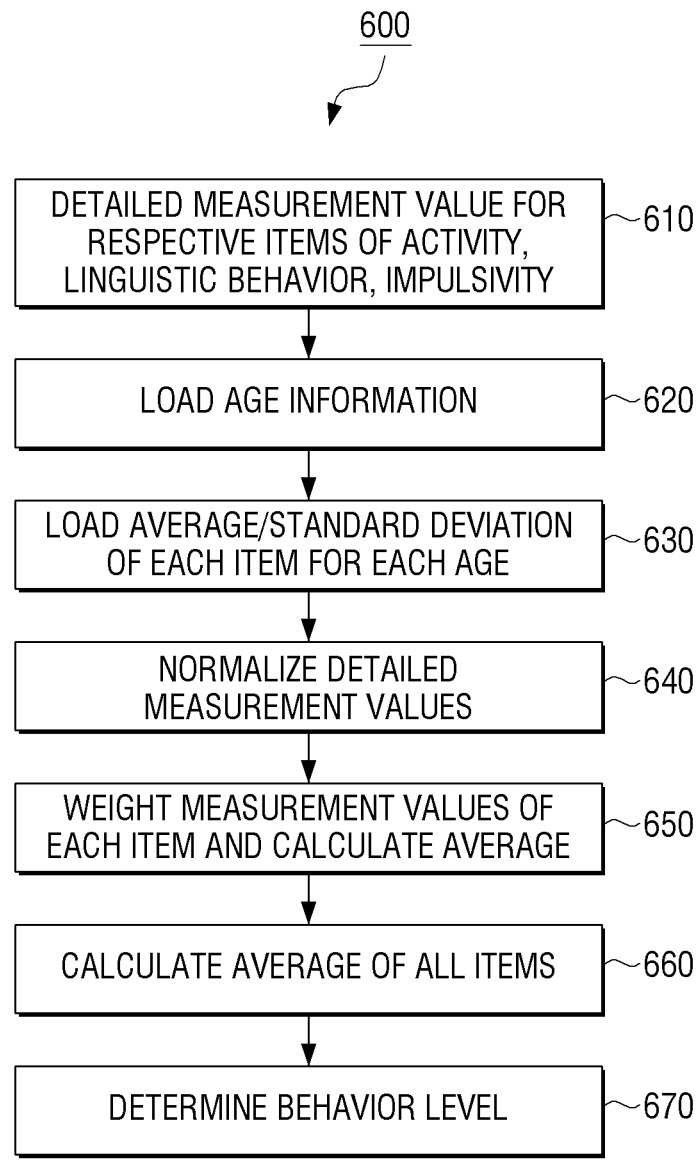
FIG. 6 is a view showing a process of determining a behavior evaluation level according to an exemplary embodiment.

FIG. 6 is a view showing a process 600 of determining a behavior evaluation level according to an exemplary embodiment.

Referring to FIG. 6, in response to detailed measurement values for the respective items of the activity item 310, the linguistic behavior item 320, and the impulsivity item 330 having been loaded at step 610, the controller 130 of FIG. 4 may load user's age information at step 620, and load an average/standard deviation of each item for each age in relation to the user's age information at step 630.

In addition, the controller 130 may normalize the detailed measurement values for the respective items at step 640. Specifically, the controller 130 may normalize the detailed measurement values for the respective items using EQN. (1) as follows:

$$\text{Normalization} = 10\left(\frac{\text{measurement value} - \text{average}}{\text{standard deviation}}\right) + 50 \quad \text{EQN. (1)}$$

That is, the controller 130 may normalize the detailed measurement values for the respective items using the detailed measurement values for the respective items, and an average and a standard deviation of each item for each age using EQN. (1).

In addition, the controller 130 may weigh the normalized measurements values for the respective items, and calculate an average at step 650. The controller 130 may weight differently according to each of the items based on a user's behavior improvement item. For example, when the behavior improvement item is the item of sleepiness during classes/study hours, the controller 130 may give relatively high weight to the activity item 310. In addition, when the behavior improvement item is the item of use of specific slang/swear word, the controller 130 may give relatively high weight to the linguistic behavior item 320. In particular, the controller 130 may weigh the detailed measurement values of each of the items using EQN. (2) as follows:

$$\text{Score}_{activity} = \frac{\sum_{k=1}^{n} W_k T_k}{n} \quad \text{EQN. (2)}$$

EQN. (2) shows a method for weighting the activity item 310 of FIG. 3, but is equally applied to the linguistic behavior item 320 of FIG. 3 and the impulsivity item 330 of FIG. 3. Specifically, the controller 130 may give a weight ($W_k$) to a value ($T_k$) which is a normalized value of a behavior pattern regarding a heart rate corresponding to the activity item 310, and add up the values during a behavior pattern measuring time and calculate an average of the detailed measurement values of the activity item 310.

In addition, the controller 130 may add up the averages of the detailed measurement values calculated for the respective items of the activity item 310, the linguistic behavior item 320, and impulsivity item 330, and calculate an average for the total items at step 660 using EQN. (3) as follows:

$$\text{Average for Total Items} = \frac{W_A \times Score_{activity} + W_L \times Score_{language} + W_I \times Score_{impulsivity}}{3} \quad \text{EQN. (3)}$$

In calculating the average for the total items, different weight may be given to each item and the average may be calculated by adding up the values.

In addition, the controller 130 may determine a user's behavior evaluation level based on the calculated average for the total items. Specifically, the controller 130 may compare the calculated average for the total items and a predetermined reference value, and determine the behavior evaluation level according to a deviation.

For example, the controller 130 may set a reference value based on the average/standard deviation of each item for each age which is loaded, and determine the reference value as indicating a normal level of a behavior evaluation level. When a behavior evaluation level having a reference value of 46-50 inclusive is determined as a normal level, the controller 130 may determine that the behavior evaluation level is very good when the average for the total items is less than or equal to 40, determine that that the behavior evaluation level is good when the average for the total items is 41-45 inclusive, and may determine that the behavior evaluation level is normal when the average for the total items is 46-50 inclusive. In addition, the controller 130 may determine that the behavior evaluation level is bad when the average for the total items is 51-55 inclusive, and determine that the behavior evaluation level is serious when the average for the total items is greater than or equal to 56. The behavior evaluation levels according to the average for the total items may be arranged as in following Table I:

TABLE I

| | Average of Total Items | | | | |
|---|---|---|---|---|---|
| | Less than or equal to 40 | 41-45 | 46-50 | 51-55 | Greater than equal to 56 |
| Behavior Evaluation Level | Very Good | Good | Normal | Bad | Serious |

Referring back to FIG. 4, the first electronic device 100 may further include the storage 150 for storing user's behavior pattern history information.

The controller 130 may determine the behavior evaluation level by measuring a similarity between the measured user's behavior pattern and the user's behavior pattern history information.

That is, when it is difficult to mathematize and digitize the measured user's behavior pattern as in FIG. 6, the user's behavior patterns collected during a predetermined period may be modeled and the user's behavior pattern history information may be stored. The controller 130 may determine the behavior evaluation level by matching the stored user's behavior pattern history information with the measured user's behavior pattern.

Figure 7:
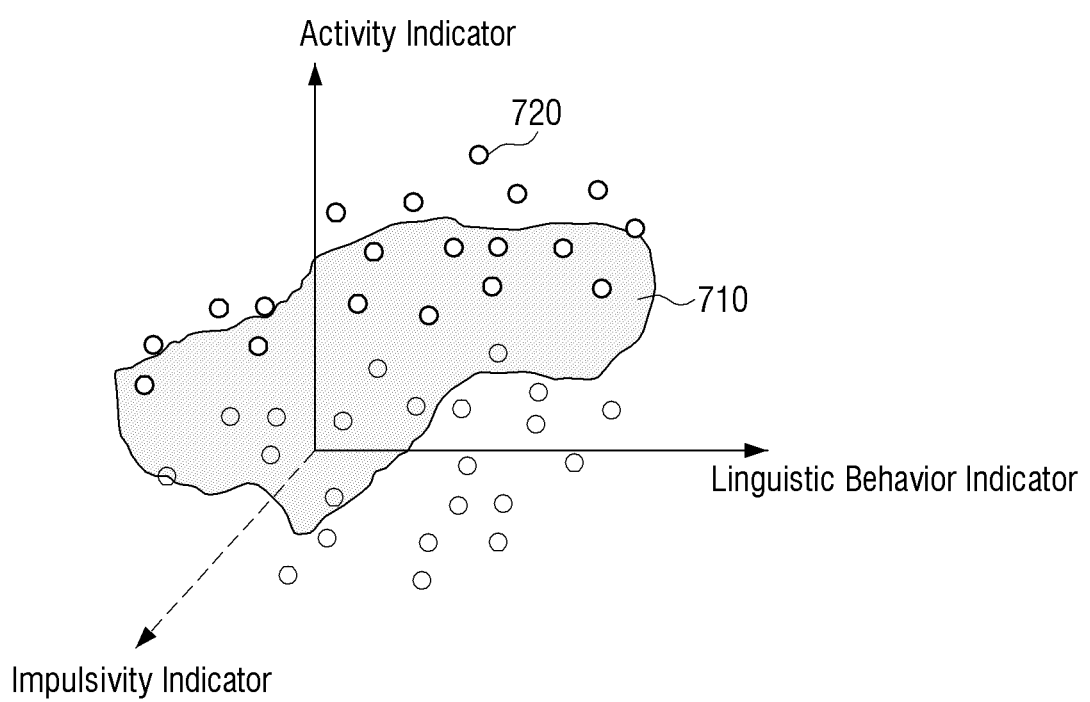
FIG. 7 is a view to illustrate a method of determining a behavior evaluation level by matching patterns according to an exemplary embodiment.

FIG. 7 is a view showing a method for determining a behavior evaluation level by matching patterns according to an exemplary embodiment.

Referring to FIG. 7, user's behavior pattern history information may be displayed on a coordinate system in which an activity indicator, an impulsivity indicator, and a linguistic behavior indicator are mapped onto the x, y, and z axes. That is, it can be understood that, in the coordinate system in which the activity indicator, the impulsivity indicator, and the linguistic behavior indicator are mapped onto the x, y, z axes, the user's behavior pattern history information is distributed in a first area 710.

In addition, when the measured user's behavior pattern is located in a second area 720 on the coordinate system, the controller 130 may compare the measured user's behavior pattern and the behavior pattern history information, determines that the user's behavior pattern regarding the activity item greatly deviates from the first area 710 where the behavior pattern history information is distributed to the higher side, and the user's behavior patterns regarding the impulsivity as discussed and the linguistic behavior item are located inside the first area 710 where the behavior pattern history information is distributed, and determine that the user's behavior evaluation level is bad.

The behavior pattern history information may be collected from a plurality of users during a predetermined period, and may be classified by age, region, country, and the like, and stored. Accordingly, the controller 130 may determine the user's behavior evaluation level by comparing a currently measured user's behavior pattern and a variety of user's behavior pattern history information for each age, region, country, and the like.

In addition, in FIG. 7, the measured user's behavior pattern and the behavior pattern history information may be displayed in view of the activity indicator, the impulsivity indicator, and the linguistic behavior indicator. However, the measured user's behavior pattern and the behavior pattern history information may be displayed by a data unit for measuring a behavior pattern such as a heart rate, a breathing rate, and the like.

In addition, the controller 130 may provide feedback according to the determined behavior evaluation level. Specifically, the controller 130 may provide feedback such as tightening a band on user's wrist or vibration according to the determined behavior evaluation level, and may provide feedback using a sound signal or an image signal.

For example, when the determined behavior evaluation level is bad, the controller 130 may tighten the band on the user's wrist or output a warning message like "You should not be doing that," or may display a GUI, and the like, showing an angry face.

In addition, when the determined behavior evaluation level is good, the controller 130 may output a positive message like "clap, clap, you are doing a good job!" display a GUI showing a smiling face, or provide feedback of adding a score on a game application.

Hereinafter, a process of providing feedback of tightening a band on user's wrist according to a determined behavior evaluation level will be explained in detail with reference to FIG. 8.

Figure 8:
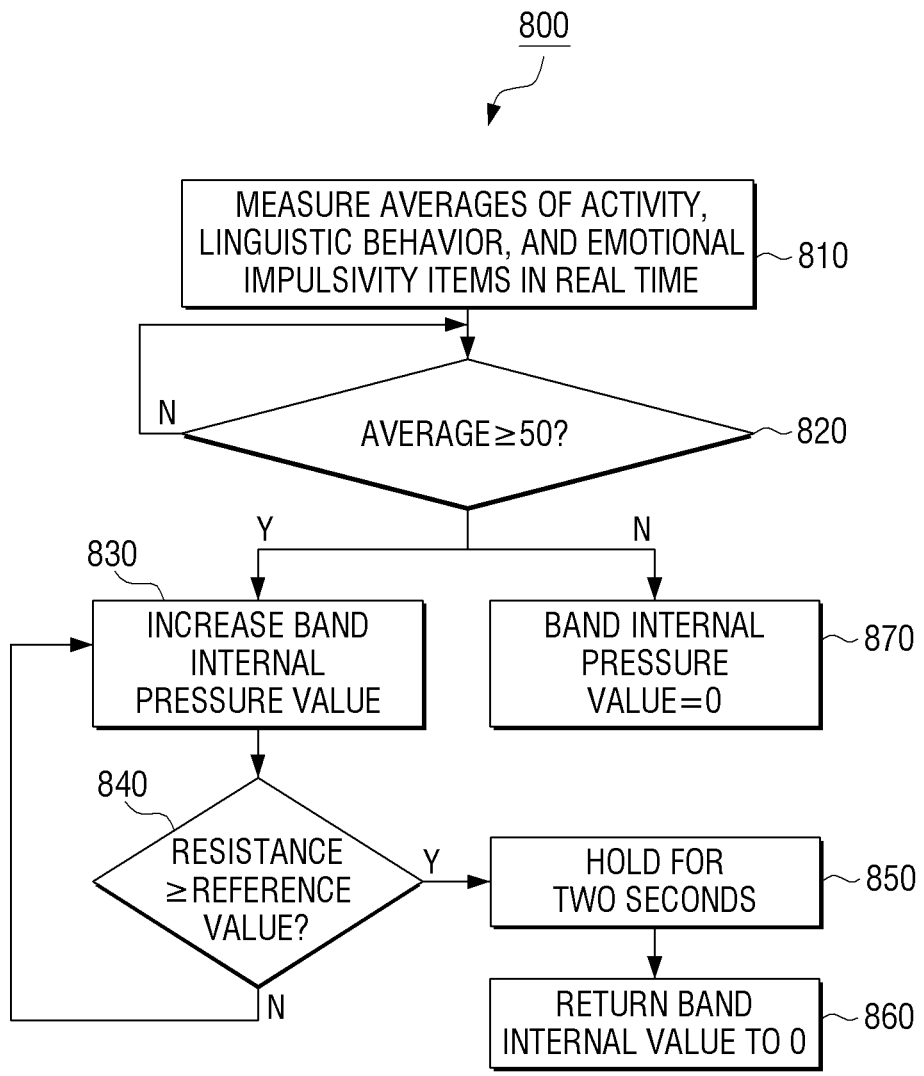
FIG. 8 is a timing chart to illustrate a process of providing band tightening feedback according to an exemplary embodiment.

FIG. 8 is a timing chart 800 to illustrate a process of providing feedback of tightening a band on user's wrist according to an exemplary embodiment.

Referring to FIG. 8, the controller 130 measures an average of the activity item 310 of FIG. 3, the linguistic behavior item 320 of FIG. 3, and the impulsivity item 330 of FIG. 3 in real time at step 810. When the average of the total items is greater than or equal to 50, the controller 130 determines that the behavior evaluation level is bad at step 820. When the average of the total items is less than or equal to 50, determines that the behavior evaluation level is not bad at step 820.

When it is determined that the behavior evaluation level is bad, the controller 130 may control a driver (not shown) to increase an internal pressure value of a band (e.g. the band 524 of FIG. 5) of a smart watch (e.g., the first electronic device 500 of FIG. 5) at step 830. The controller 130 may determine whether a resistance value exceeds a reference value at step 840. When the resistance value does not exceed the reference value, the controller 130 may control the driver (not shown) to continue increasing the band internal pressure value of the smart watch, and, when the resistance value exceeds the reference value, the controller 130 may hold the internal pressure value of the band of the smart watch for 2 seconds at step 850. The controller 130 may then return the internal pressure value of the band to 0 at step 860, thereby loosening the band from the user's wrist.

In addition, when it is determined that the behavior evaluation level is not bad, the controller 130 may maintain the internal pressure value of the band of the smart watch as 0 at step 870.

In addition, although not shown in FIG. 8, the controller 130 may increase the internal pressure value of the band of the smart watch differently according to the determined behavior evaluation level. For example, when it is determined that the behavior evaluation level is bad, the controller 130 may control the driver (not shown) to increase the band internal pressure value of the smart watch up to 5, and, when it is determined that the behavior evaluation level is serious, the controller 130 may control the driver (not shown) to increase the band internal pressure value of the smart watch up to 10.

Figure 9:
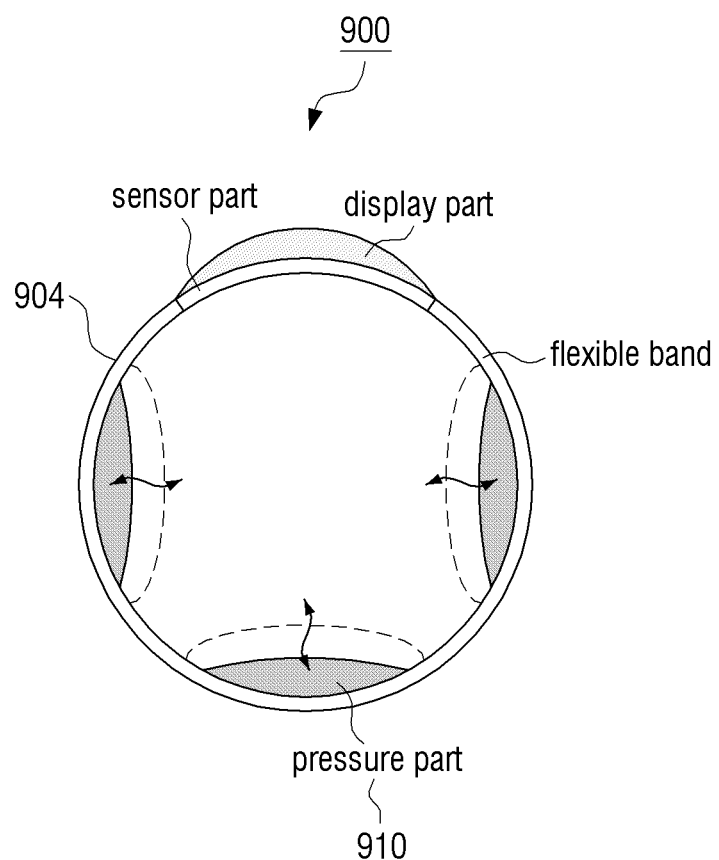
FIGS. 9 and 10 are views showing a physical configuration for implementing a band tightening feedback effect according to an exemplary embodiment.
Figure 10:
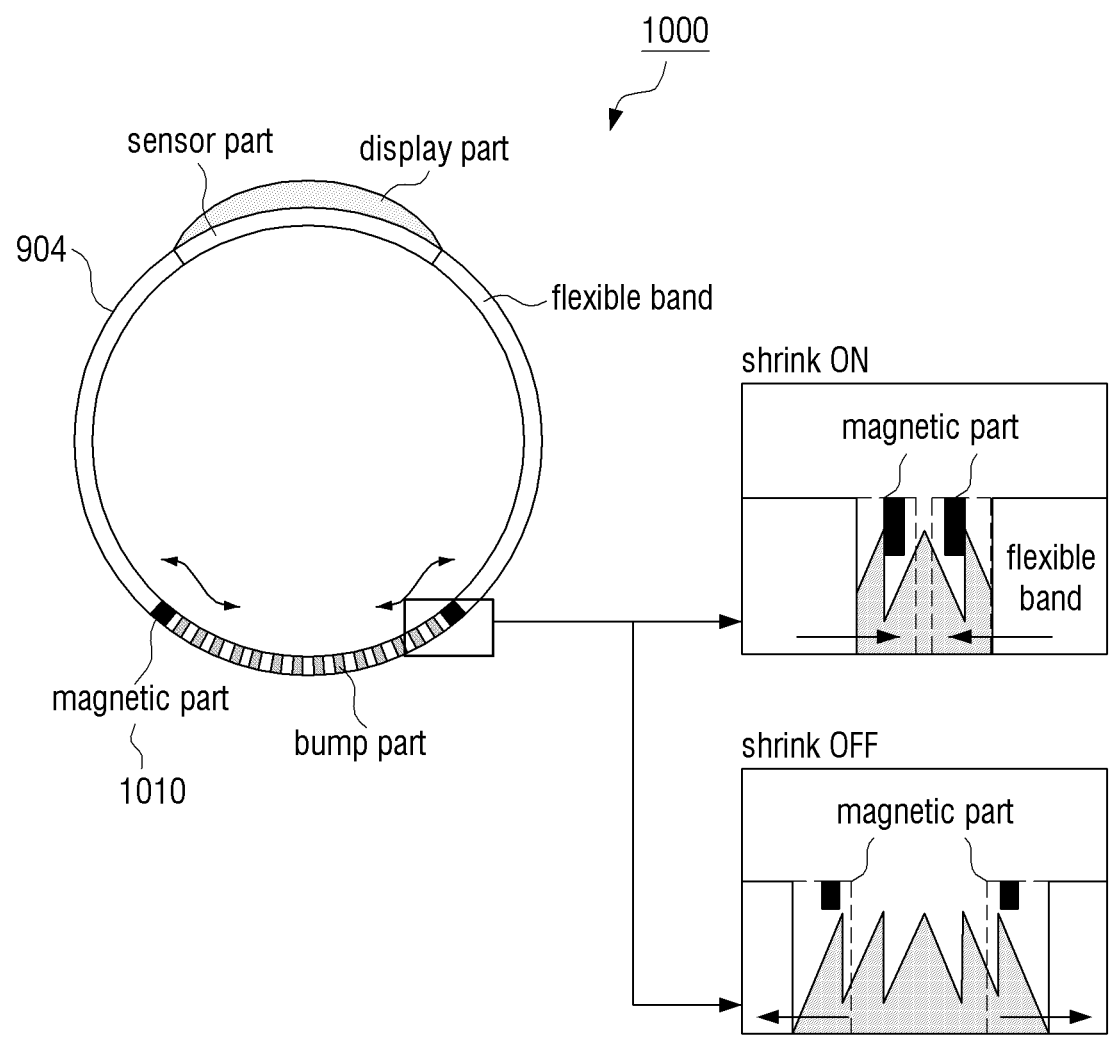

FIGS. 9 and 10 are views showing respective physical configurations 900, 1000 for implementing a feedback effect of tightening a band 904 on user's wrist according to an exemplary embodiment.

Referring to FIG. 9, a band tightening effect may be implemented by adjusting air pressure inside the band 904 of a smart watch using a pressure sensor 910.

In addition, referring to FIG. 10, the band tightening effect may be implemented by using magnetic characteristics of a magnet 1010. As implemented in FIGS. 9 and 10, the controller 130 may provide the banding tightening effect directly to the user by adjusting air pressure or a magnetic force differently according to the determined behavior evaluation level. Such a band tightening effect is not notified to a third person and is provided only to the user, so that the user can improve user's behaviors in user's own way through the feedback.

In the exemplary embodiment of FIGS. 8 through 10, the controller 130 provides direct feedback to the user according to the determined behavior evaluation level. However, the controller 130 may provide feedback to the user by interworking with the second electronic device.

Specifically, the controller 130 may transmit control information to a second electronic device (not shown) to control the second electronic device to operate under a usage environment which is set according to the determined behavior evaluation level. The usage environment refers to an available time and an available content set for respective second electronic devices.

In particular, the controller 130 may generate control information corresponding to the determined behavior evaluation level. Regarding this, the storage 150 of the first electronic device 100 may include data necessary to generate the control information.

Specifically, data necessary to generate the control information may include at least one of a type of the second electronic device, an available time of the second electronic device according to the behavior evaluation level, a type of content reproducible in the second electronic device according to the behavior evaluation level, control information for controlling the second electronic device, and login information of a user for the second electronic device. Such data may be arranged in a lookup table and stored in the storage 150 as a database. Accordingly, in response to the behavior evaluation level and the type of the second electronic device, which establishes a communication session by pairing with the first electronic device 100 or performs user authentication, having been determined, the controller 130 may select, from a lookup table, the available time of the second electronic device according to the behavior evaluation level, a type of content reproducible in the second electronic device according to the behavior evaluation level, the control information to control the second electronic device, based on the behavior evaluation level and the type of the second electronic device. The controller 130 may also generate control information including detailed values regarding the type of the second electronic device, the available time of the second electronic device according to the behavior evaluation level, the type of content reproducible in the second electronic device according to the behavior evaluation level, the control information for controlling the second electronic device, and the login information of the user for the second electronic device.

In addition, in response to the user's behavior evaluation level and the type of the second electronic device having been determined, the controller 130 may determine the available time of the second electronic device, the type of the reproducible content, the control information, and the like, according to the determined behavior evaluation level through a predetermined calculation method, without using the lookup table stored in the storage 150.

For example, in response to the type of the second electronic device having been determined to be a TV, the controller 130 may calculate the available time (0 minute, a minimum setting time, minimum setting time+0.5*(maximum setting time-minimum setting time), minimum setting time+0.8*(maximum setting time-minimum setting time), and a maximum setting time) of the TV through a predetermined calculation method in response to the user's behavior evaluation level (serious, bad, normal, good, and very good).

In addition, the controller 130 may determine the type of the reproducible content (unallowable, minimum allowable channels, 50% channels allowable, 80% channels allowable, maximum allowable channels) through a predetermined calculation method in response to the user's behavior evaluation level (serious, bad, normal, good, and very good).

As described above, the controller 130 may generate the control information through the pre-stored database, generate the control information through the predetermined calculation method, and also generate the control information using every possible method. Of course, the user or a third person may directly set the available time item of the second electronic device, the type of the reproducible content, and the like, of the control information. Hereinafter, various examples of control information will be explained.

That is, the control information may include at least one of the available time information of the respective second electronic devices, available content information, and a control command for controlling the second electronic device to operate according the available time information and the available content information. In addition, the available time information of the second electronic device and the information on the content available in the second electronic device may be changed according to the determined behavior evaluation level. That is, the available time range of the second electronic device may increase or decrease, and the number of content types available in the second electronic device may increase or decrease according to the determined behavior evaluation level.

For example, the controller 130 may transmit control information to a TV to allow the user to watch the TV for 60 minutes a day according to a determined behavior evaluation level. The control information may include the available time "60 minutes," which is set to operate the TV, and a control command to operate the TV for 60 minutes, that is, an execution word or command.

Such control information may be implemented in the form of a table in which data is stored as shown in Table II presented below:

TABLE II

| Device | Available Time | Content | Control Command |
|--------|----------------|---------|-----------------|
| TV | 60 minutes | — | Execute Operation and Finish Operation |

In addition, the controller 130 may transmit, to an HMD device, control information for allowing the user to use the HMD device for 70 minutes a day according to a determined behavior evaluation level. Likewise, the control information may include the available time "70 minutes," which is set to operate the HMD device, and a control command to operate the HMD device for 70 minutes, that is, an execution word or command.

As described above, such control information may be implemented in the form of a table in which data is stored as shown in Table III presented below:

TABLE III

| Device | Available Time | Content | Control Command |
|--------|----------------|---------|-----------------|
| HMD Device | 70 minutes | — | Execute Operation and Finish Operation |

In addition, the controller 130 may transmit, to a TV, control information for allowing the user to watch only an education broadcast outputted from channel 00 through the TV. Herein, the control information may include the available "70 minutes," which is set to operate the TV, a control command to control the TV to operate for 70 minutes, information indicating that the content available in the TV is limited to the education broadcast, and a control command to control the TV to provide only the education broadcast, that is, an execution word or command.

Likewise, the control information may be implemented in the form of a table in which data is stored as shown in Table IV presented below:

TABLE IV

| Device | Available Time | Content | Control Command |
|--------|----------------|---------|-----------------|
| TV | 70 minutes | Education Broadcast outputted from channel 00 | Execute Operation and Finish Operation |

In addition, when the control information on a plurality of second electronic devices indicates that the user has watched a TV for 60 minutes and has used an HMD device for 70 minutes during 130 minutes a day, for example, the controller 130 may transmit, to the TV and the HMD device, control information to allow the user to watch the TV for 80 minutes and to use the HMD device for 50 minutes during 130 minutes a day according to a determined behavior evaluation level. Herein, the control information may include available time information indicating that 80 minutes are set to operate the TV, and 50 minutes are set to operate the HMD device, and a control command to control the TV and the HMD device to operate for 80 minutes and 50 minutes, respectively, that is, an execution word or command.

Likewise, the control information may be implemented in the form of a table in which data is stored as shown in Table V presented below:

TABLE V

| Device | Available Time | Content | Control Command |
|--------|----------------|---------|-----------------|
| TV | 80 minutes | — | Execute Operation and Finish Operation |
| HMD Device | 50 minutes | — | Execute Operation and Finish Operation |

In addition, when it is determined that the behavior evaluation level determined is very good, the controller 130 may transmit control information to the TV to allow the user to play a game for 100 minutes through the TV. When it is determined that the behavior evaluation level determined is good, the controller 130 may transmit control information to the TV to allow the user to watch an animation for 50 minutes through the TV and to play a game for 50 minutes. In addition, when it is determined that the behavior evaluation level determined is normal, the controller 130 may transmit control information to the TV to allow the user to watch an animation for 50 minutes through the TV and to watch an education broadcast for 50 minutes through the TV. In addition, when it is determined that the behavior evaluation level determined is bad, the controller 130 may transmit control information to the TV to allow the user to watch only an education broadcast for 100 minutes through the TV. When it is determined that the behavior evaluation level determined is serious, the controller 130 may transmit control information to the TV to prohibit the user from watching the TV.

As described above, the controller 130 may transmit the control information to at least one second electronic device to control the at least one second electronic device or a plurality of second electronic devices to operate in a differently set usage environment according to a behavior evaluation level determined.

In addition, in the above-described examples, the control information includes the available time information and the available content information on the respective second electronic devices. However, this should not be considered as limiting, and the control information may include information on a limitation in functions executable in the second electronic device, and also include information on various usage environments.

FIG. 11 is a view showing various examples of usage environments included in the control information according to an exemplary embodiment.

Referring to FIG. 11, the usage environments for a smartphone/tablet (console), an HMD, a PC, and a TV may be determined differently according to a behavior evaluation level. Specifically, the applicability of restricted items may vary according to control information corresponding to a determined behavior evaluation level and the smartphone/tablet (console). For example, when the behavior evaluation level is good or very good and thus a reward is needed, an login allowance item, an content type extend item, a usage time increase item, a cyber money increase item, and a data capacity increase item may be applied to the smartphone/tablet (console). In addition, when the behavior evaluation level is bad or serious and thus a punishment is needed, a login disallowance item, a content type restriction item, a usage time reduction item, a cyber money reduction item, and a data capacity reduction item may be applied to the smartphone/tablet (console).

The detailed usage environment applied to the smartphone/tablet (console) based on restriction items may vary according to the behavior evaluation level.

For example, when the behavior evaluation level is serious, a usage environment in which the smartphone/tablet (console) provides only a basic function such as calling or texting may be set for the smartphone/tablet (console). When the behavior evaluation level is bad, a usage environment in which the smartphone/tablet (console) provides a designated training content, restricts movement between contents to allow the user to watch only the designated training content, and the user is allowed to use an Internet browser application for 20 minutes and use a music application for 1 hour may be set for the smartphone/tablet (console).

In addition, when the behavior evaluation level is normal, a usage environment in which the smartphone/tablet (console) provides a training content option to allow the user to select a training content, and the user is allowed to use an Internet browser application for 40 minutes, use a music application for 2 hours, use a social networking service (SNS) application for 20 minutes, and use one application included in a wish list for 1 hour may be set for the smartphone/tablet (console).

In addition, when the behavior evaluation level is good, a usage environment in which the smartphone/tablet (console) allows the user to use contents or applications for 5 hours regardless of their types without limitation, and provides cyber money of 15,000 won may be set for the smartphone/tablet (console).

In addition, when the behavior evaluation level is very good, a usage environment in which the smartphone/tablet (console) allows the user to use without any limitation, and provides cyber money of 20,000 won may be set for the smartphone/tablet (console).

As described above, the usage environment for separately restricting the usage time of the second electronic device, the type of content, the type of application, the amount of cyber money, and the like, according to a behavior evaluation level may be set for the second electronic device. Likewise, the usage environment for separately restricting the usage time, the type of content, the type of application, the amount of cyber money, and the like, according to a behavior evaluation level may be set for the other second electronic devices, such as an HMD device, a PC/laptop, a TV.

In addition, the usage environment which is set for each of the second electronic devices according to a behavior evaluation level as shown in FIG. 11 may be included in the control information. In response to the control information having been transmitted to the second electronic device by the controller 130, the second electronic device may operate under the usage environment set as shown in FIG. 11.

In response to the user of the first electronic device 100 performing user authentication with respect to the second electronic device, the controller 130 may transmit the control information to the second electronic device. Specifically, after the user of the first electronic device 100 performs user authentication with respect to the second electronic device, the controller 130 may transmit the control information to the authenticated second electronic device to control the authenticated second electronic device to operate under the usage environment which is set according to the behavior evaluation level determined.

The user authentication refers to a process of identifying, by the user wearing the first electronic device 100, the user himself/herself with respect to an electronic device to use the electronic device. Various exemplary embodiments for identifying a user himself/herself with respect to an electronic device will be explained in detail below.

After the user authentication is performed, the second electronic device may receive the control information for setting the usage environment which is determined according to the behavior evaluation level of the authenticated user, and operate for the authenticated user under the usage environment corresponding to the control information.

When the user wishes to perform user authentication with respect to the second electronic device, the user may use the first electronic device 100 that the user wears. Specifically, the first electronic device 100 may perform user authentication by communicating with the second electronic device through a short-range wireless communication method (Bluetooth, WiFi, NFC, Infrared Data Association (IrDA). For example, in response to the first electronic device 100 of FIG. 1 transmitting encrypted information to a second electronic device (not shown) through a short-range wireless communication method, the second electronic device may process the encrypted information and compare the information with stored information. When the information is identical to the stored information, the user authentication is achieved.

In addition, when the user wishes to perform user authentication with respect to the second electronic device, the first electronic device 100 may perform user authentication using fingerprint recognition, iris recognition, face recognition, ECG recognition detected through a finger ECG sensor, recognition of a user's own voice using a microphone, recognition of a personal gait pattern detected using an acceleration sensor or a camera. For example, the user may perform user authentication with respect to a smartphone through fingerprint recognition, and perform user authentication through face recognition through a camera installed in a TV. In addition, the user may perform user authentication through iris recognition for a virtual reality (VR) device.

In addition, the user may not perform user authentication with respect to the second electronic device. Instead, the user may perform user recognition with respect to the TV by performing fingerprint recognition through a fingerprint recognition sensor (not shown) provided on a remote controller (not shown), and may perform user recognition with respect to the TV by performing face recognition through a camera (not shown) provided on the remote controller.

Alternatively, the first electronic device 100 may transmit the control information to the second electronic device without performing user authentication. That is, only when the user of the first electronic device 100 performs user authentication with respect to the second electronic device, the controller 130 may transmit the control information to the second electronic device. However, when the first electronic device 100 enters a predetermined range from the second electronic device, the first electronic device 100 may automatically transmit the control information to the second electronic device without requiring the user of the first electronic device 100 to perform user authentication with respect to the second electronic device.

For example, when the user carrying or wearing the first electronic device 100 enters a predetermined range from the second electronic device, the first electronic device 100 may detect the second electronic device via a wireless communication method or through the sensor 110. Accordingly, the controller 130 may transmit control information corresponding to the detected second electronic device to the second electronic device. Accordingly, even when the user carrying or wearing the first electronic device 100 does not perform user authentication with respect to the second electronic device, the second electronic device may operate based on the control information received from the first electronic device 100.

In particular, in response to the second electronic device having been detected, the controller 130 may establish a communication session by pairing the first electronic device 100 with the detected second electronic device. Herein, a communication establishing operation between the first electronic device 100 and the second electronic device may be defined as pairing, and the pairing may be performed through WiFi, WiFi Direct, Bluetooth, and the like. In addition, the controller 130 may establish a communication session to perform communication smoothly with an external device by performing pairing with the second electronic device. In addition, the controller 130 may transmit the generated control information to the second electronic device.

Herein, the controller 130 may establish the communication session by pairing the first electronic device 100 with some or all of the detected second electronic devices. However, the controller 130 may establish the communication session by pairing the first electronic device 100 with only the second electronic device that requests control information from the first electronic device 100 from among the detected second electronic devices.

The controller 130 may transmit, to the second electronic device paired with the first electronic device 100, a control signal for displaying an image regarding the user through the second electronic device paired with the first electronic device 100 according to a determined behavior evaluation level.

Specifically, when it is determined that the behavior evaluation level determined is bad or serious, the controller 130 may record an image of the user and store the image in the storage 150 of FIG. 3, and may transmit information on the image on the user to the paired second electronic device and transmit the control signal for displaying the image of the user on the paired second electronic device.

Accordingly, a third person may reproduce and monitor the image of the user stored in the storage 150 of the first electronic device 100, and also, may view and monitor the image of the user transmitted from the first electronic device 100 in real time through the second electronic device.

In addition, when the second electronic device exists within a predetermined range from the first electronic device 100, the first electronic device 100 is automatically paired with the second electronic device and thus the controller 130 may automatically transmit the control signal for displaying the image on the user through the second electronic device to the second electronic device.

In addition, the controller 130 may transmit the information on the image of the user to another second electronic device to store the same in the second electronic device, and may transmit the information on the image on the user to a server (not shown) to store the same in the server.

In FIGS. 1 through 11, in response to a behavior improvement item having been set, the first electronic device 100 detects data for measuring a user's behavior pattern, measures the user's behavior pattern, determines a behavior evaluation level based on the measured behavior pattern, and provides feedback to the user according to the determined behavior evaluation level, provides a service by interworking with an external device, or provides a service of monitoring a degree of behavior improvement. However, the functions of determining the behavior evaluation level based on the measured behavior pattern, and providing the service by interworking the second electronic device according to the determined behavior evaluation level, or providing the service of monitoring the degree of behavior improvement may be performed in a server (not shown). That is, the first electronic device 100 may measure the user's behavior pattern, determine the behavior evaluation level, and provide feedback to the user by interworking with the server, or may provide the service or provide the service of monitoring a degree of behavior improvement via interworking with the second electronic device. In addition, the first electronic device 100 may transmit, to the server, all pieces of information on the data for measuring the user's behavior pattern, the measured user's behavior pattern, the determined user's behavior evaluation level, and the control information for controlling the second electronic device to operate in the usage environment set according to the determined behavior evaluation level, and store the information in the server.

Figure 12A:
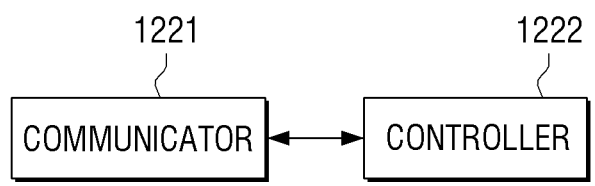
FIG. 12A is a block diagram showing a configuration of a server according to an exemplary embodiment.

FIG. 12A is a block diagram showing a configuration of a server 1220 according to an exemplary embodiment.

Referring to FIG. 12A, the server 1220 includes a communicator 1221 and a controller 1222. The server 1220 recited herein is generally computer hardware in which a server program is executed. According to an exemplary embodiment, the server 1220 determines a user's behavior evaluation level based on biological signals acquired in the above-described electronic device, generates control information corresponding to the behavior evaluation level, establishes a communication session by pairing the server

1220 with a second electronic device (not shown), and transmit control information to the second electronic device.

Specifically, the communicator 1221 may communicate with a first electronic device and a second electronic device. The first electronic device and the second electronic device may correspond to the electronic device 100 as described above and an external electronic device, respectively. The first electronic device and the second electronic device may establish the communication session via pairing with the communicator 1221 of the server 1220 through WiFi or an Access Point (AP).

In addition, the controller 1222 may determine a user's behavior evaluation level based on biological signals received from the first electronic device 100. In response to information on the second electronic device paired with the first electronic device 100 having been received from at least one of the first electronic device and the second electronic device, the controller 1222 may determine control information corresponding to the behavior evaluation level and the information on the second electronic device, and control to transmit the determined control information to the second electronic device.

The communicator 1221 may receive user's biological signals from the first electronic device 100. That is, in response to user's biological signals having been acquired through the sensor 110 provided in the first electronic device 100. In turn, the first electronic device 100 may transmit the acquired biological signals to the server 1220. Accordingly, the communicator 1221 of the server 1220 may receive the biological signals from the first electronic device 100.

In addition, the controller 1222 may determine a user's behavior evaluation level based on the received biological signals, generate control information corresponding to the behavior evaluation level, establish a communication session with the second electronic device, and control to transmit the control information to the second electronic device.

Herein, the processes of: determining the user's behavior evaluation level based on the received biological signals; generating the control information corresponding the behavior evaluation level; establishing the communication session with the second electronic device; and transmitting the control information to the second electronic device, and the detailed configuration of the control information have been described in the above explanation of the first electronic device 100, and are equally applied.

Figure 12B:
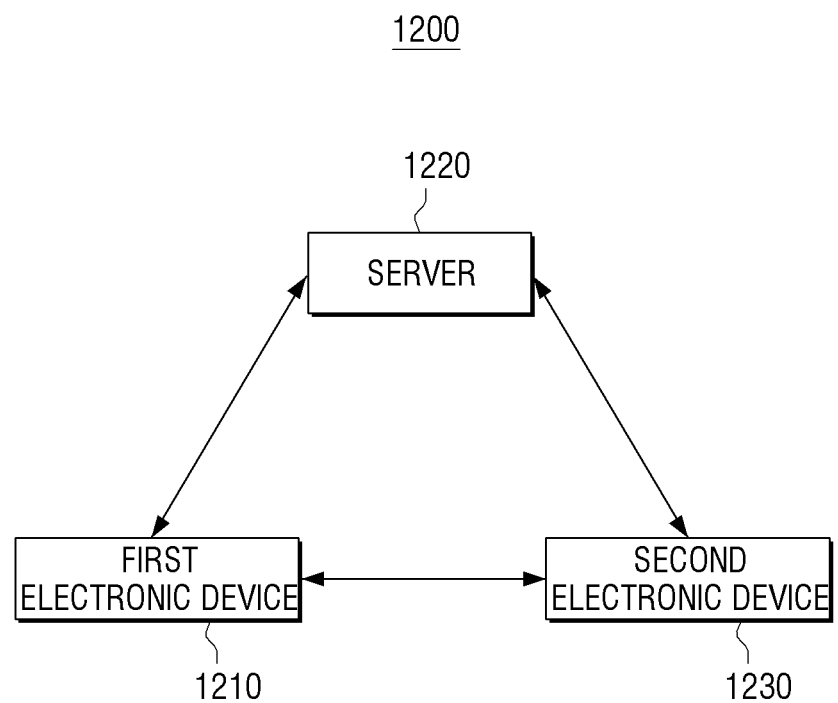
FIG. 12B is a view showing a system which includes a first electronic device, a second electronic device, and a server according to an exemplary embodiment.

FIG. 12B is a view showing a system 1200 including a first electronic device 1210, a second electronic device 1230, and a server according to an exemplary embodiment.

The system 1200 includes the first electronic device 1210, the server 1220, and the second electronic device 1230. The first electronic device 1210 detects data to measure a user's behavior pattern, determines a user's behavior evaluation level based on the user's behavior pattern measured based on the detected data, and transmits control information to the server 1220 to control the second electronic device 1230 to operate in a usage environment which is set according to the behavior evaluation level determined.

In addition, in response to the user performing user authentication with respect to the second electronic device 1230, the server 1220 may transmit the control information to the second electronic device 1230.

In addition, the second electronic device 1230 may operate for the authenticated user based on the control information received from the server 1220.

The first electronic device 1210 may detect data to measure the user's behavior pattern and then transmit the detected data to the server 1220. In addition, the server 1220 may measure the user's behavior pattern based on the data for measuring the user's behavior pattern, which is detected in the first electronic device 1210. In addition, the server 1220 may determine the user's behavior evaluation level based on the user's behavior pattern measured, and transmit information on the user's behavior evaluation level determined to the first electronic device 1210. In addition, the first electronic device 1210 may provide direct feedback to the user based on the information on the user's behavior evaluation level, and the server 1220 may transmit the control information to the second electronic device 1230 to control the second electronic device 1230 to operate in the usage environment which is set according to the behavior evaluation level determined. Specifically, in response to the information on the second electronic device paired with the first electronic device 1210 having been received from at least one of the first electronic device 1210 and the second electronic device 1230, the server 1220 may determine the control information corresponding to the behavior evaluation level and the information on the second electronic device, and transmit the control information determined to the second electronic device 1230.

The server 1220 may transmit the control information to the second electronic device 1230 only when the user performs user authentication with respect to the second electronic device 1230. In addition, only when the user performs user authentication, the second electronic device 1230 may receive the control information from the server 1220 and operate in the usage environment set according to the behavior evaluation level based on the received control information. Of course, the second electronic device 1230 may transmit a signal for directly requesting the control information to the server 1220 only when the user performs user authentication.

The interworking process among the first electronic device 1210, the server 1220, and the second electronic device 1230 will be explained in detail below with reference to FIG. 13.

Figure 13:
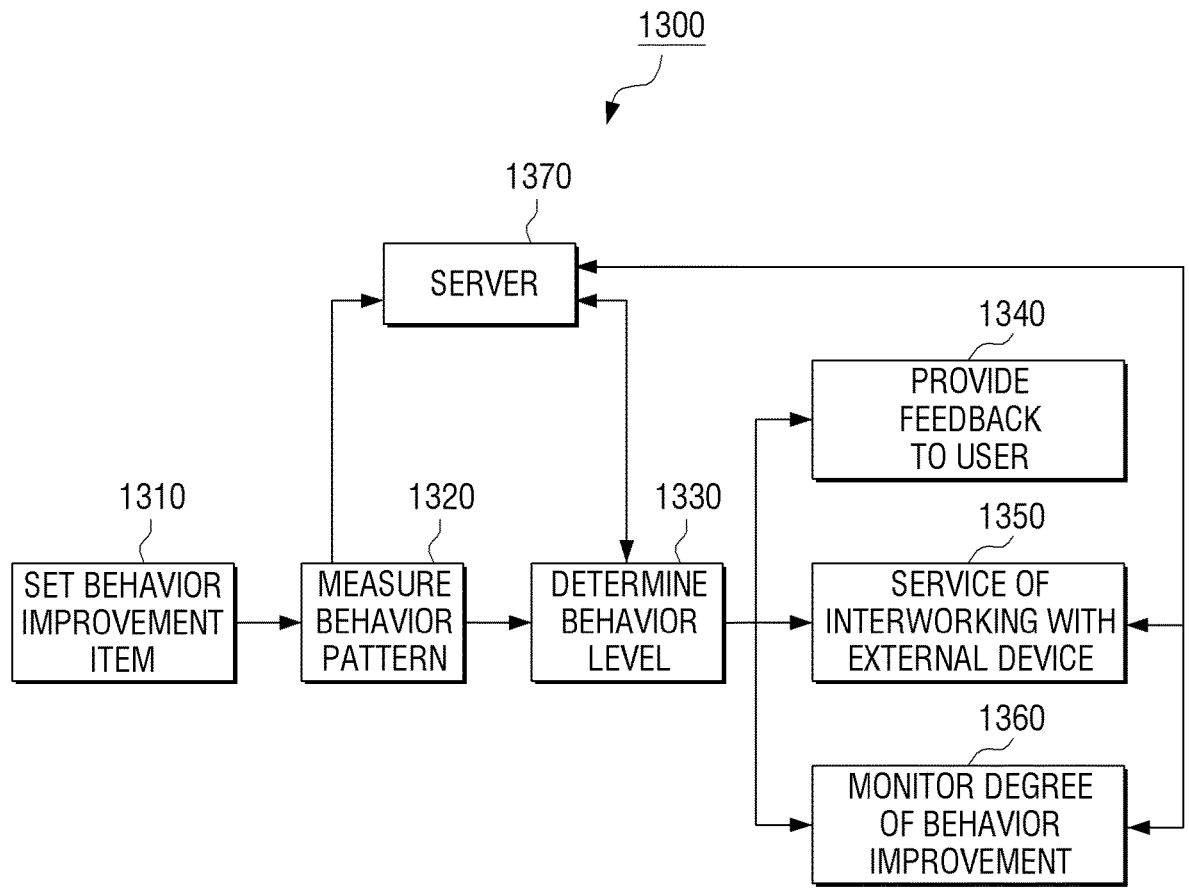
FIG. 13 is a view showing a process performed in the system including the first electronic device, the server, and the second electronic device of FIG. 12B according to an exemplary embodiment.

FIG. 13 is a view showing a process 1300 which is performed in the system 1200 of FIG. 12B including the first electronic device 1210 of FIG. 12, a server 1370 (which may be similar to the server 1220 of FIG. 12), and the second electronic device 1230 of FIG. 12 according to an exemplary embodiment. Herein, the first electronic device 1210 is the same as the first electronic device 100 (e.g., of FIG. 3), and accordingly, the elements included in the first electronic device 1210 are the same as those of the first electronic device 100.

Referring to FIG. 13, in response to a behavior improvement item having been set at operation 1310, the sensor 110 of the first electronic device 1210 may detect data for measuring a user's behavior pattern, and the controller 130 may measure a user's behavior pattern based on the detected data at operation 1320, and transmit the measured user's behavior pattern to the server 1370. In addition, the controller 130 may transmit the detected data to the server 1370, and the server 1370 may measure the user's behavior pattern based on the detected data.

In addition, the controller 130 may determine a user's behavior evaluation level based on the measured user's behavior pattern at operation 1330, and transmit information on the determined behavior evaluation level to the server 1370. Likewise, when the server 1370 measures the user's behavior pattern based on the detected data, the server 1370 may determine the user's behavior evaluation level based on the measured user's behavior pattern, and transmit information on the user's behavior evaluation level determined to the first electronic device 1210.

In addition, the controller 130 may provide feedback to the user according to the behavior evaluation level determined at step 1340, and transmit control information to the second electronic device 1230 for controlling the second electronic device 1230 to operate in a usage environment which is set according to the behavior evaluation level determined, and control the second electronic device 1230 to operate in the usage environment set according to the behavior evaluation level determined, thereby providing a behavior improvement service by interworking the external device at step 1350. In addition, the controller 130 may transmit, to the second electronic device 1230, information on the result of monitoring the degree of behavior improvement, for example, information on a recorded image or a real-time image on the user.

In addition, the controller 130 may provide feedback to the user according to the determined behavior evaluation level at step 1340, and the server 1370 may transmit, to the second electronic device 1230, the control information for controlling the second electronic device 1230 to operate in the usage environment which is set according to the behavior evaluation level determined, and control the second electronic device 1230 to operate in the usage environment set according to the behavior evaluation level determined, thereby providing the behavior improvement service by interworking the external device at step 1350. In addition, the server 1370 may transmit, to the second electronic device 1230, information on the result of monitoring the degree of behavior improvement, for example, information on a recorded image or a real-time image on the user.

The server 1370 may generate behavior pattern history information based on the detected data for measuring the user's behavior pattern, which is received from the first electronic device 1210, and the user's behavior pattern, and may establish a database by classifying the behavior pattern history information by age, region, and country based on the detected data for measuring behavior patterns of a plurality of users, and the behavior patterns.

In addition, in response to the usage environment of the second electronic device 1230 having been set to be changed according to the determined behavior evaluation level, the server 1370 may change and update the control information in response to the change, or may establish a database for each user based on the changed control information.

According to an exemplary embodiment, the first electronic device 100 may be used to automatically recognize an attention-deficit/hyperactivity disorder (ADHD) symptom and provide feedback to alleviate the symptom.

The ADHD symptom is a disorder which mainly appears during childhood, and refers to a state in which a person continuously lacks attention and concentration, is hyperactive, and shows impulsivity. Therefore, the ADHD symptom shows symptoms such as lack of attention, impulsivity, hyperactivity, and the like.

Accordingly, when a user having the ADHD symptom wears the first electronic device 100, the sensor 110 of the first electronic device 100 may detect data on a heart rate, a breathing rate, a moving distance, the number of steps, a holding time of each type of motion (running, walking, or sitting), the number of times of finger movements, a voice volume, a speaking time, a crying time, the number of times of using a specific word, the number of times of interrupting a talk, a holding time of an emotional state (excitement or anger), and the number of times of changing an emotional state of the user, and the controller 130 may measure a user's behavior pattern based on the detected data. In addition, the controller 130 may determine a user's behavior evaluation level based on the behavior pattern measured as shown in FIG. 6. As described above about the process 600 of determining the behavior evaluation level, the behavior evaluation level of the user having the ADHD symptom may be divided into levels, "very good," "good," "normal," "bad," and "serious," and, as described above, the controller 130 may provide feedback according to the behavior evaluation level determined, for example, by tightening a band on user's wrist, or provide feedback using a sound signal or an image signal, and may transmit control information to the second electronic device for controlling the second electronic device, for which user authentication is performed by the user having the ADHD symptom, to operate in a usage environment which is set according to the determined behavior evaluation level. Specifically, the controller 130 may perform pairing with the second electronic device, determine control information corresponding to the behavior evaluation level and the paired second electronic device, and transmit the control information determined to the paired second electronic device. In addition, the controller 130 may transmit, to the second electronic device, a control signal for displaying an image on the user having the ADHD symptom through the second electronic device according to the determined behavior evaluation level, and controls to monitor.

In addition, as described above, by interworking with each other, the first electronic device 100 and the server 1220 may measure the behavior pattern of the user having the ADHD symptom, determine the behavior evaluation level based on the measured behavior pattern, and provide feedback to the user having the ADHD symptom according to the determined behavior evaluation level, transmit, to the second electronic device, the control information for controlling the second electronic device to operate in the usage environment set according to the determined behavior evaluation level, thereby providing a behavior improvement service by interworking with the second electronic device, or record the image of the user having the ADHD symptom and transmit the recorded image to an external device or transmit the image of the user having the ADHD symptom to the second electronic device in real time, thereby providing a monitoring service.

The operations and functions performed in the first electronic device 100, 1210, the server 1220, and the second electronic device 1230, and the data, control information, and the like, thereof as described above with reference to FIGS. 1 through 13 may be equally applied to the user having the ADHD symptom.

Meanwhile, when the user having the ADHD symptom uses the second electronic device 1230 which operates in the usage environment set based on the received control information, the first electronic device 100, 1210 may detect and analyze data indicating whether the user having the ADHD symptom accepts the usage environment of the second electronic device 1230 and behaves thereunder.

For example, the first electronic device 100, 1210 may measure the brainwave of the user having the ADHD symptom, who uses the second electronic device 1230 operating in the usage environment set based on the received control information, and analyze a brainwave indicator related to attention and concentration, and may detect whether the user implements a training content provided by the second electronic device 1230 and determine whether the user's behavior is improved or not.

In addition, the first electronic device 100, 1210 may determine the behavior of the user having the ADHD symptom when the user uses the second electronic device 1230 by detecting the number of times of moving a menu in the second electronic device 1230, the number of times of resetting a program, the number of times of wearing or taking off the second electronic device 1230 such as an HMD device, and the like.

In addition, the first electronic device 100, 1210 may determine the behavior of the user having the ADHD symptom when the user uses the second electronic device 1230 by detecting a time during which the user stays one content from among the contents provided by the second electronic device 1230, the number of times of hopping between the contents per unit time, and the like.

In addition, the first electronic device 100, 1210 may determine the behavior of the user having the ADHD symptom when the user uses the second electronic device 1230 by determining a gaze fixing ability using gaze tracking information of the user having the ADHD symptom and also determining an ability to refrain from gazing at an unnecessary object.

In the above-described examples, the first electronic device 100, 1210 determines the biological signals, motion, and training content implementing ability of the user having the ADHD symptom when the user uses the second electronic device 1230, but the second electronic device 1230 may determine the biological signals, motion, and training content implementing ability of the user having the ADHD symptom.

Figure 14:
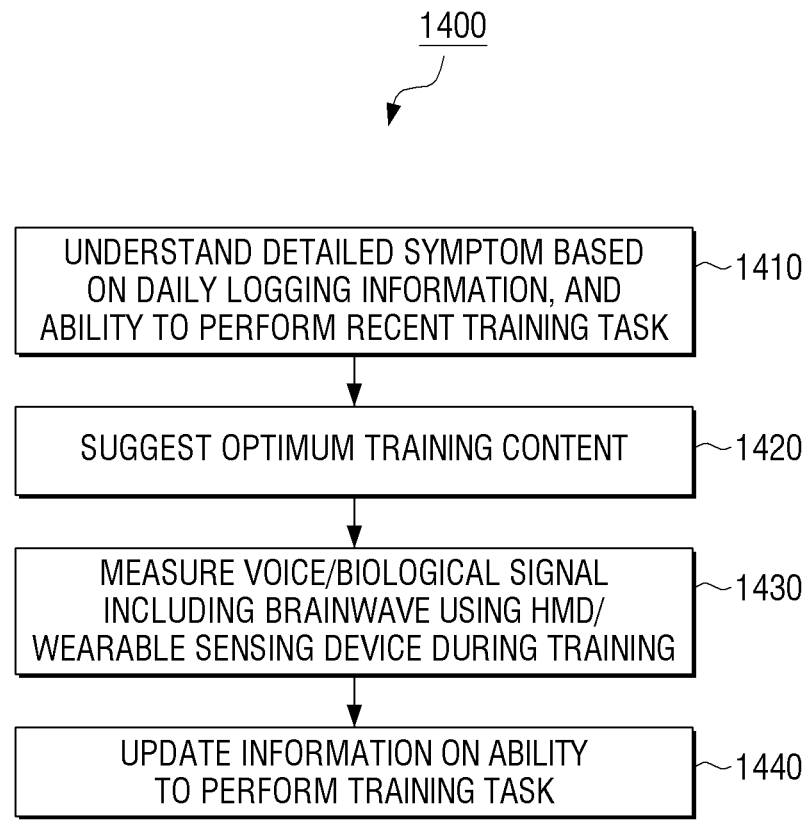
FIG. 14 is a view showing processes of determining a user's implementing ability when a user having the attention deficit hyperactivity disorder (ADHD) symptom uses the second electronic device, and determining whether user's behavior is improved or not.

FIG. 14 is a view showing a process 1400 of determining a user's implementing ability when the user having the ADHD symptom uses the second electronic device, and determining whether the user's behavior is improved or not according to an exemplary embodiment.

Referring to FIG. 14, the first electronic device 100 understands details in the state of the user having the ADHD symptom based on daily logging information of the user regarding the second electronic device and the latest training task achievement ability at step 1410.

In addition, the first electronic device 100 determines an optimum training content based on the details in the state of the user having the ADHD symptom, and transmits a control signal for providing the optimum training content to the second electronic device at step 1420.

Thereafter, the first electronic device 100 may detect the brainwave, voice, motion, and biological signals of the user having the ADHD symptom while the user implements the training content provided by the second electronic device at step 1430.

In addition, the first electronic device 100 may determine the user's training content implementing ability based on the brainwave, voice, motion, and biological signals of the user having the ADHD symptom, and update information on the training content implementing ability at step 1440. The server 200 may update while continuously storing the information on the training content implementing ability of the user having the ADHD symptom.

Accordingly, the first electronic device 100 may determine the training content implementing ability of the user having the ADHD symptom through the training content provided by the second electronic device, and update the information on the training content implementing ability.

The first electronic device 100 may acquire user's biological signals during a predetermined period (1 day or 1 week), determine the user's behavior pattern based on the acquired biological signals, and then automatically select an ADHD symptom improvement item from the determined behavior pattern. That is, when the user uses the first electronic device 100 during a predetermined period while carrying the first electronic device 100, the first electronic device 100 may acquire the user's biological signals during the predetermined period and automatically determine the ADHD symptom improvement item based on the acquired user's biological signals even when the user or a third person does not directly input the ADHD symptom improvement item through the first electronic device 100 or another electronic device. For example, the first electronic device 100 may select items "the user lacks attention and concentration during classes/study hours," "the user is hyperactive during classes/study hours," "the user's mood swings are bad," and the like, as the ADHD symptom improvement items based on the user's biological signals.

In addition, the first electronic device 100 may acquire the user's biological signals in relation to the selected improvement items, and determine a user's behavior evaluation level based on the user's biological signals acquired. Herein, the first electronic device 100 may determine not only the user's behavior evaluation level but also a new target behavior evaluation level based on the behavior evaluation level determined.

Accordingly, when the user's behavior evaluation level exceeds a predetermined range with reference to the newly set target behavior evaluation level, the first electronic device 100 may provide an effect of tightening a band on user's wrist or provide feedback to the user by interworking with the second electronic device via adjusting the available time of the second electronic device or the type of content provided by the second electronic device. As described above, the first electronic device 100 newly sets the target behavior evaluation level, compares the currently determined user's behavior evaluation level with the newly set target behavior evaluation level, and provides feedback to the user, thereby improving the user's behavior continuously.

In the above explanation, the process 1400 of determining a behavior level has been described. Hereinafter, the process of determining a behavior level in relation to the ADHD symptom will be explained in detail.

Specifically, the controller 130 determines a behavior level by comparing an average calculated for each item with a predetermined reference value. For example, the predetermined reference value may refer to a standard deviation between a value of a normal range and an average of a normal range.

For example, it is assumed that, as a predetermined reference value, a normal range average regarding the heart rate of the activity item is 85 and a standard deviation, which is estimated to be within a normal range, is 10, and a normal range average regarding the number of steps is 5000 and a standard deviation which is estimated to be within a normal range is 700. In this state, when the measured user's average heart rate is 95 and the measured average number of steps of the user is 4000, the controller 130 may calculate an average corresponding to the average heart rate measured as 60, and calculate an average value corresponding to the average number of steps measured as 64, considering the normal range average and the standard deviation.

In addition, the controller 130 may calculate an average regarding the activity item as 60, based on the average of 60 corresponding to the average heart rate measured and the average of 64 corresponding to the average number of steps measured.

In addition, it is assumed that, as a predetermined reference value, a normal range average regarding the speaking time of the linguistic behavior item is 180 minutes, and a standard deviation which is estimated to be within a normal range is 60 minutes. In this case, when the user's speaking time measured is 300 minutes, the controller 130 may calculate an average corresponding to the user's speaking time as 70, considering the normal range average and the standard deviation.

In addition, the controller 130 may calculate an average regarding the linguistic behavior item as 65 based on the average corresponding to the measured speaking time.

In addition, the controller 130 may give different weight to an item according to whether the item needs more improvement or according to importance. For example, the controller 130 may give weight to the activity item, the linguistic behavior item, and the impulsivity in the form of 1.1:1.0:1.2. That is, the controller 130 gives relatively higher weight to the activity item and the impulsivity item than the linguistic behavior item because it is regarded that the activity item and the impulsivity item need more improvement.

Thereafter, the controller 130 may calculate an average of the total items based on the weight given to the respective items. This is the same as described above and thus a detailed description is omitted.

Figure 15:
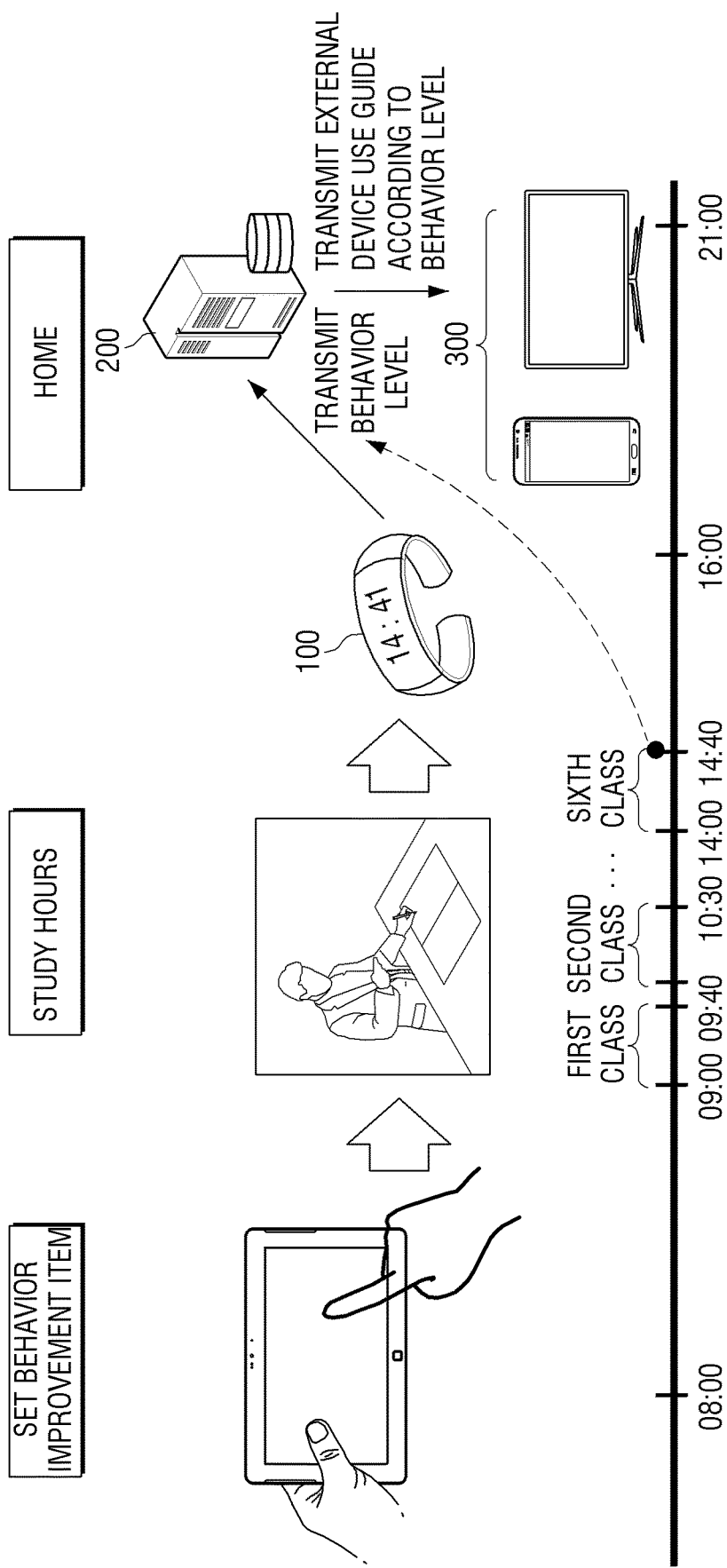
FIG. 15 is a view to illustrate a case in which an electronic device is used in daily life according to an exemplary embodiment.

FIG. 15 is a view to illustrate a situation in which the first electronic device 100 is used in daily life according to an exemplary embodiment.

Referring to FIG. 15, the parent of the user may select a behavior improvement item at 8:00 a.m. Specifically, the behavior improvement item may include an item of attention and concentration during classes/study hours, an item of sleepiness during classes/study hours, an item of hyperactivity in a seat during classes/study hours, an item of use of specific slang/swear word, an item of crying loudly or shouting, and the like, and the parent of the user may select one of them.

In addition, the first electronic device 100 detects data for measuring a user's behavior pattern related to the selected behavior improvement item. In particular, the first electronic device 100 may detect the data for measuring the user's behavior pattern related to the selected behavior improvement item according to a set behavior pattern measuring time.

For example, when the set behavior pattern measuring time is school hours, the first electronic device 100 may accumulatively detect the data for measuring the user's behavior pattern related to the selected behavior improvement from the 1$^{st}$ class period to the 6$^{th}$ class period, which are school hours, that is, from 9:00 a.m. to 2:40 p.m.

In addition, the first electronic device 100 determines a user's behavior evaluation level based on the accumulatively detected data, and transmits the determined behavior evaluation level to the server 200 at a predetermined time.

The first electronic device 100 may continue determining the user's behavior evaluation level based on the detected data, and accordingly, may provide feedback such as tightening a band on user's wrist to the user when the user's behavior evaluation level exceeds a reference value.

Thereafter, when the user comes back home after school hours, and performs user authentication with respect to a smartphone or a TV, the server 200 may transmit, to the smartphone or the TV, control information for controlling the smartphone or the TV to operate in a usage environment which is set according to the determined behavior evaluation level.

Accordingly, when the user's behavior evaluation level is determined to be bad, the usage environment is set such that the usage time of the smartphone or the TV is reduced, and, when the user's behavior evaluation level is determined to be good, the usage environment is set such that the usage time of the smartphone or the TV increases.

The electronic device according to an exemplary embodiment may be used to improve a problem of lack of exercise of a user. The user or a third person may set a target exercising time or target calories to be burned through the electronic device or another electronic device. For example, the user or third person may input a numerical value for each of items which are measurable in daily life. For example, the user or third person may input the numerical values through the first electronic device 100 or another electronic device, in the form of "walking up and down stairs 200 times," "walking 1000 steps," and "running 500 meters."

As described above, when the numerical values for the respective items, walking up and down stairs, walking, and running, are inputted, the first electronic device 100 may measure a user's average heart rate in daily life when the user initially uses the first electronic device 100. In the case of children, it is known that the average heart rate in daily life is 80-90 beats per minute.

In addition, the first electronic device 100 may store the user's average heart rate measured and then measure user's activity only when the user's heart rate exceeds the average heart rate. That is, when the user's average heart rate measured is 90 and the user's heart rate is greater than or equal to 90, the first electronic device 100 measures the user's activity. This is to exclude a case in which the user just shakes the first electronic device 100 while sitting still from the measurement of the activity, and thus measures the user's activity more exactly. When the user's hear rate is greater than or equal to 90, the first electronic device 100 may measure the user's activity for each type of motion (walking up and down stairs, walking, or running) using an acceleration sensor or a gyro sensor. The first electronic device 100 may calculate burned calories based on the measured user's activity.

Thereafter, the first electronic device 100 may check whether the user's target exercise is achieved or not or whether the target calories are burned or not during a predetermined period by comparing the user's target exercising time or target calories to be burned, and also, may calculate an achievement rate for each of the items (walking up and down stairs, walking, or running). In addition, the first electronic device 100 may calculate the achievement rate of each of the items by percent, and provide the result of calculating to the user with respective percent sections. For example, the first electronic device 100 may divide the achievement rate of each item into a section less than or equal to 50 percent, a section of 50-80 percent, a section of 80-100 percent, a section of 100-120 percent, and a section greater than or equal to 120 percent, and provide the result to the user. In addition, as described above, the first electronic device 100 may provide direct feedback (e.g., tightening a band on user's wrist) to the user differently according to each of the percent sections, and may provide feedback to the user by interworking with the second electronic device by adjusting the available time of the second electronic device (a mobile phone, a TV, an HMD device, and the like) or the type of content provided by the second electronic device.

In addition, the processes of: checking whether the user's target exercise is achieved or not or whether the target calories are burned or not during a predetermined period by comparing the user's target exercising time or target calories to be burned; calculating an achievement rate for each of the items (walking up and down stairs, walking, or running);

and calculating the achievement rate of each of the items by percent, and providing the result of calculating to the user with respective percent sections may be performed in the server 200. Meanwhile, the electronic device according to an exemplary embodiment may be used to improve linguistic habits.

The user may directly input language that the user wishes to improve through the electronic device or another electronic device in the form of a text or voice recording, and the first electronic device 100 may monitor language that the user utters through a microphone during a predetermined period, select meaningless language which is frequently used, and generate a list of language.

In addition, when the language directly inputted by the user or the language selected as a result of monitoring is set to language to be improved, and the user uses the set language when speaking, the first electronic device 100 may record a corresponding section and count the number of times the set language is used.

In addition, when the number of times the set language is used exceeds a predetermined number, the first electronic device 100 may provide direct feedback (e.g., tightening a band on user's wrist, an image signal, voice signal, and the like) to the user.

In addition, the first electronic device 100 may transmit, to the second electronic device, a recorded file in which the set language is recorded when the same is used, or information on the number of times the set language is used, and the second electronic device may display the number of times the language selected to be improved is used, reproduce the recorded language, or reproduce use history, and the like, based on the recorded file or the number of times of using, thereby allowing the user to monitor. Accordingly, the user can monitor user's linguistic habits during a predetermined time through the second electronic device.

In addition, when the user exercises a presentation, the user may set the first electronic device 100 to operate in a habit improvement mode in order to monitor user's behavior habits in a short period, and the first electronic device 100 records the language that the user uses or counts the number of times of using until the first electronic device 100 is released from the habit improvement mode. Accordingly, the first electronic device 100 may record the language used by the user or count the number of times of using only when the habit improvement mode is turned on, and provide the relevant information to the second electronic device, thereby allowing the user to monitor the information and thus monitor the user's behavior habits during a short period.

When the target permissible number of times of using the language set to be improved is 5 per day, the electronic device 100 may measure the number of times the set language is used in the language uttered by the user, and calculate the same by percent based on the measured number of times of using the language and the target permissible number of times.

Figure 16:
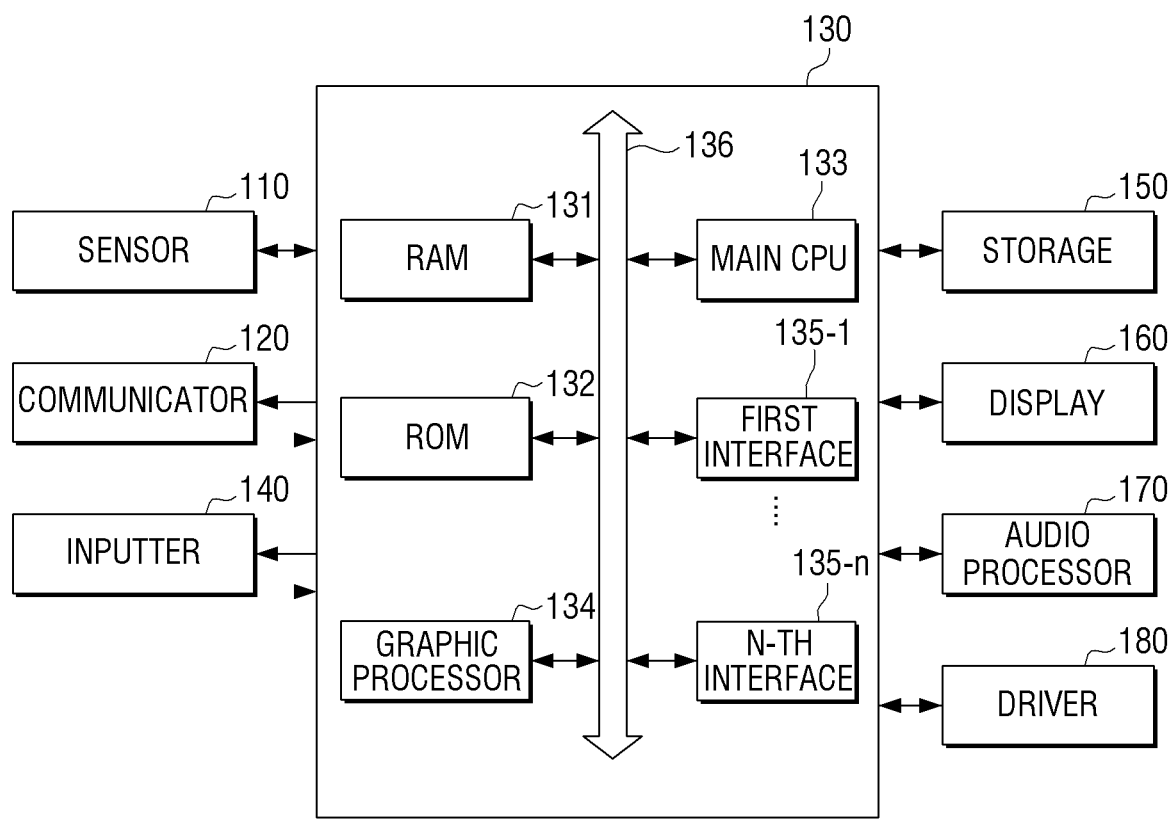
FIG. 16 is a block diagram showing a detailed configuration of the electronic device shown in FIG. 1.

FIG. 16 is a block diagram showing the detailed configuration of the first electronic device 100 shown in FIG. 1

Referring to FIG. 16, the first electronic device 100 includes a sensor 110, a communicator 120, a controller 130, an input 140, a storage 150, a display 160, an audio processor 170, and a driver 180. Although not shown in the drawing, the first electronic device 100 may further include a speaker (not shown). The same elements in FIG. 16 as those shown in FIGS. 1 and 4 are not described in detail.

The controller 130 may control the overall operations of the first electronic device 100.

Specifically, the controller 130 may include a Random-Access-Memory (RAM) 131, a Read-Only-Memory (ROM) 132, a main Central Processing Unit (CPU) or main CPU 133, a graphic processor 134, first to n-th interfaces 135-1 to 135-$n$, and a bus 136.

The RAM 131, the ROM 132, the main CPU 133, the graphic processor 134, and the first to n-th interfaces 135-1 to 135-$n$ may be connected with one another via the bus 136.

The first to n-th interfaces 135-1 to 135-$n$ may be connected with the above-described various elements. One of the interfaces may be a network interface which is connected with an external device via a network.

The main CPU 133 may access the storage 150 and perform booting using an operating system (O/S) stored in the storage 150. In addition, the main CPU 133 may perform various operations using various programs, content, data, and the like, which are stored in the storage 150.

The ROM 132 may store a set of instructions for booting a system. In response to a turn on command having been inputted and power having been supplied, the main CPU 133 may copy the O/S stored in the storage 150 into the RAM 131 according to a command stored in the ROM 132, and boot the system by executing the O/S. In response to the booting having been completed, the main CPU 133 may copy various application programs stored in the storage 150 into the RAM 131, and perform various operations by executing the application programs copied into the RAM 131.

The graphic processor 134 may generate a screen including various objects such as an icon, an image, a text, and the like, using a calculator (not shown) and a renderer (not shown). The calculator (not shown) may calculate attribute values of objects to be displayed according to a layout of the screen, such as a coordinate value, a shape, a size, a color, and the like, based on a received control command. The renderer (not shown) may generate the screen of various layouts including objects based on the attribute values calculated by the calculator (not shown). The screen generated by the renderer (not shown) may be displayed through the display 160.

The operations of the controller 130 described above in FIGS. 1 through 15 may be achieved by a program stored in the storage 150.

The storage 150 may store an O/S software module for driving the first electronic device 100, and a variety of data such as various multimedia contents.

In particular, the storage 150 may include various software modules for controlling the controller 130 to determine a user's behavior evaluation level based on biological signals, specifically, measure a user's behavior pattern based on detected data, determine a user's behavior evaluation level based on the measured behavior pattern, perform pairing with a second electronic device, determine control information corresponding to the behavior evaluation level and the second electronic device, and transmit the determined control information to the second electronic device. These operations will be explained in detail below with reference to FIG. 17.

The audio processor 170 may process audio signals according to user's settings on an output rage of the speaker and sound quality.

In addition, the driver 180 may implement a band tightening effect by adjusting air pressure inside the band using a pressure sensor 910 provided on the band of the first electronic device 100, or using magnetic characteristic of a magnet 1010.

Figure 17:
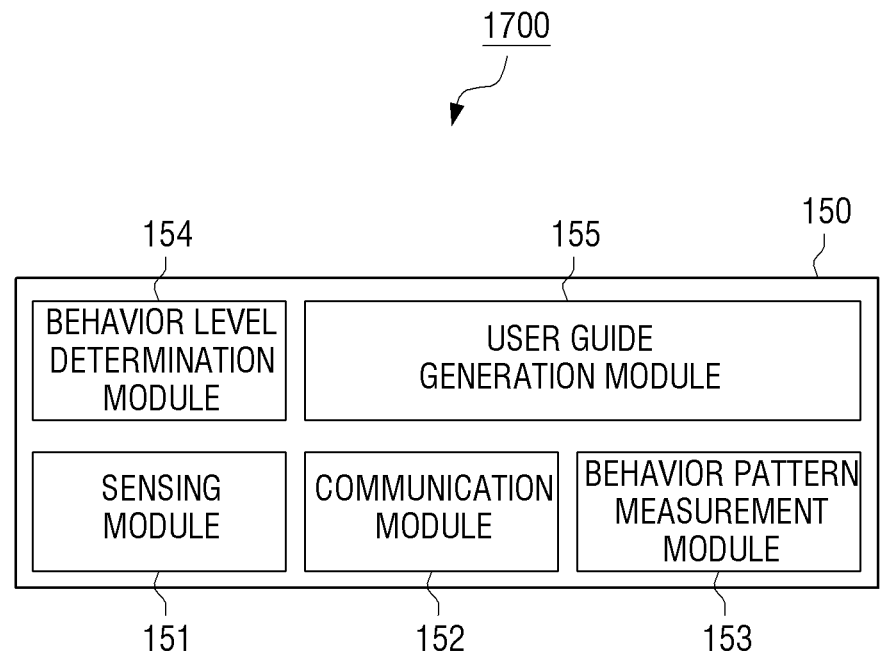
FIG. 17 is a view showing software modules stored in a storage according to an exemplary embodiment.

FIG. 17 is a view showing software modules 1700 which are stored in the storage according to an exemplary embodiment.

Referring to FIG. 17, the storage 150 may store programs such as a sensing module 151, a communication module 152, a behavior pattern measurement module 153, a behavior evaluation level determination module 154, and a control information generation module 155.

The above-described operations of the controller 130 may be performed by the programs stored in the storage 150. Hereinafter, the detailed operations of the controller 130 using the programs stored in the storage 150 will be explained in detail.

The sensing module 151 is a module for collecting information from various sensors, and analyzing and managing the collected information. Specifically, the sensing module 151 may collect data for measuring a user's behavior pattern, and analyze and manage sensing values. The sensing module 142 may include a biological signal recognition module, a touch recognition module, a head direction recognition module, a face recognition module, a voice recognition module, a motion recognition module, an NFC recognition module, a brainwave recognition module, an emotion state recognition module, and the like.

The communication module 152 is a module for communicating with or performing pairing with the second electronic device. The communication module 152 may include a device module which is used to communicate with an external device, a messaging module such as a messenger program, Short Message Service (SMS) and Multimedia Message Service (MMS) programs, an email program, and the like, and a telephony module including a call info aggregator program module, an VoIP module, and the like.

The behavior pattern measurement module 153 may perform a function of measuring a user's behavior pattern based on detected data.

The behavior evaluation level determination module 154 may perform a function of determining a user's behavior evaluation level based on the measured user's behavior pattern. As explained in FIG. 6, the behavior evaluation level determination module 154 may perform functions of calculating an average for total items using EQN. (1), EQN. (2), and EQN. (3), and determining a behavior evaluation level according to a deviation by comparing the average for the total items and a predetermined reference value, or determining a behavior evaluation level by matching the measured user's behavior pattern with user's behavior pattern history information stored.

The control information generation module 155 may perform a function of generating control information for controlling the second electronic device to operate in a usage environment which is set according to the determined behavior evaluation level. The control information may include information on a usage environment which varies according to the behavior evaluation level and the type of the second electronic device, as described in FIG. 11.

Figure 18:
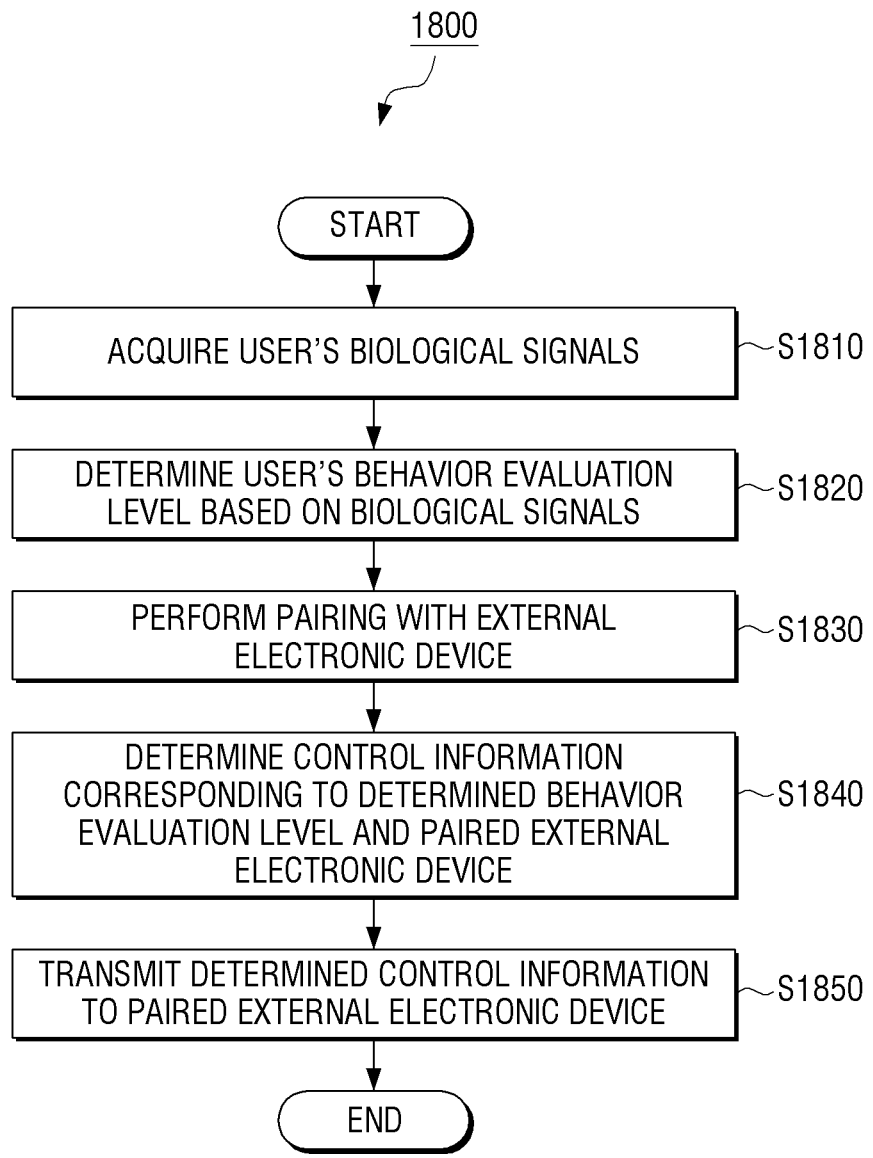
FIG. 18 is a flowchart to illustrate a control method of an electronic device according to an exemplary embodiment.

FIG. 18 is a flowchart 1800 to illustrate a control method of a first electronic device 100 (of FIG. 16) according to an exemplary embodiment.

According to the control method of the first electronic device 100 shown in FIG. 18, the first electronic device 100 acquires user's biological signals at step S1810.

The first electronic device 100 determines a user's behavior evaluation level based on the biological signals at step S1820.

Thereafter, the first electronic device 100 performs pairing with the second electronic device at step S1830.

Then, the first electronic device 100 determines control information corresponding to the determined behavior evaluation level and the paired second electronic device at step S1840.

The control information may include information on a using range of the second electronic device, and control information for controlling the second electronic device to operate based on the information on the using range. In particular, the control information may include at least one of available time information, available content information, and a control command regarding the second electronic device.

In addition, the behavior evaluation level may be determined based on a value which is calculated by digitizing the acquired biological signals according to respective items. That is, the behavior evaluation level may be determined based on a value which is calculated by digitizing the acquired biological signals by weighting at least one of activity, linguistic behavior, and impulsivities.

In addition, the using range of the second electronic device may include at least one of a predetermined condition, a predetermined range, and a predetermined mode in which the second electronic device operates in response to the behavior evaluation level.

In addition, the available time information, the available content information, and the control command regarding the second electronic device may be changed according to the determined behavior evaluation level.

Thereafter, the first electronic device 100 may transmit the determined control information to the paired second electronic device at step S1850.

In response to the user of the first electronic device 100 performing user authentication with respect to the paired second electronic device, the step of transmitting at step S1850 may transmit the control information to the second electronic device. The step of transmitting at step S1850 may transmit the control information to the second electronic device when the first electronic device 100 establishes a communication session with the second electronic device by performing pairing with the second electronic device, without requiring the user of the first electronic device 100 to perform user authentication with respect to the second electronic device.

In addition, the control method of the first electronic device according to an exemplary embodiment may further include providing feedback according to the determined behavior evaluation level.

In addition, the control method of the first electronic device 100 according to an exemplary embodiment may further include receiving an input of user manipulation to set a behavior improvement item of the user and a behavior pattern measuring time, and the step of acquiring the biological signals at step S1810 may determine a behavior pattern related to the set item and detect data for measuring the determined behavior pattern according to the set time.

In addition, the step of determining S1820 may group the measured user's behavior patterns to predetermined items, calculate an average by weighting the grouped user's behavior patterns according to each of the items, and determine a behavior evaluation level based on the calculated average.

The step of determining the behavior evaluation level S1820 may compare the calculated average and a predetermined reference value and determines the behavior evaluation level according to a deviation.

In addition, the control method of the first electronic device 100 according to an exemplary embodiment may further include storing behavior pattern history information of the user, and the step of determining the behavior evaluation level S1820 may determine the behavior evaluation level by measuring a similarity between the measured user's behavior pattern and the behavior pattern history information of the user.

In addition, the control method of the first electronic device 100 according to an exemplary embodiment may further include transmitting, to the paired second electronic device, a control signal for displaying an image on the user through the paired second electronic device according to the determined behavior evaluation level.

FIGS. 19 through 22 are timing charts to illustrate an operation process according to various exemplary embodiments. In particular, in FIGS. 19 through 22, the first electronic device 100 refers to a wearable device, and the second electronic device refers to an external device which exists outside the wearable device. A mobile device will be explained as an example of a device which selects a behavior improvement item by interworking with the wearable device. In addition, the methods illustrated in FIGS. 19 through 22 do not include the process of performing user authentication. However, the user authentication may be performed with respect to an external device, and may be performed regardless of whether the user authentication is performed before or after the interworking process among the external device and other electronic devices, that is, among the wearable device, the server, the mobile device, and the like.

In addition, in FIGS. 19 through 22, dots are displayed to clearly indicate a connection state between electronic devices. That is, the dots indicate that communication is established between electronic devices.

Figure 19:
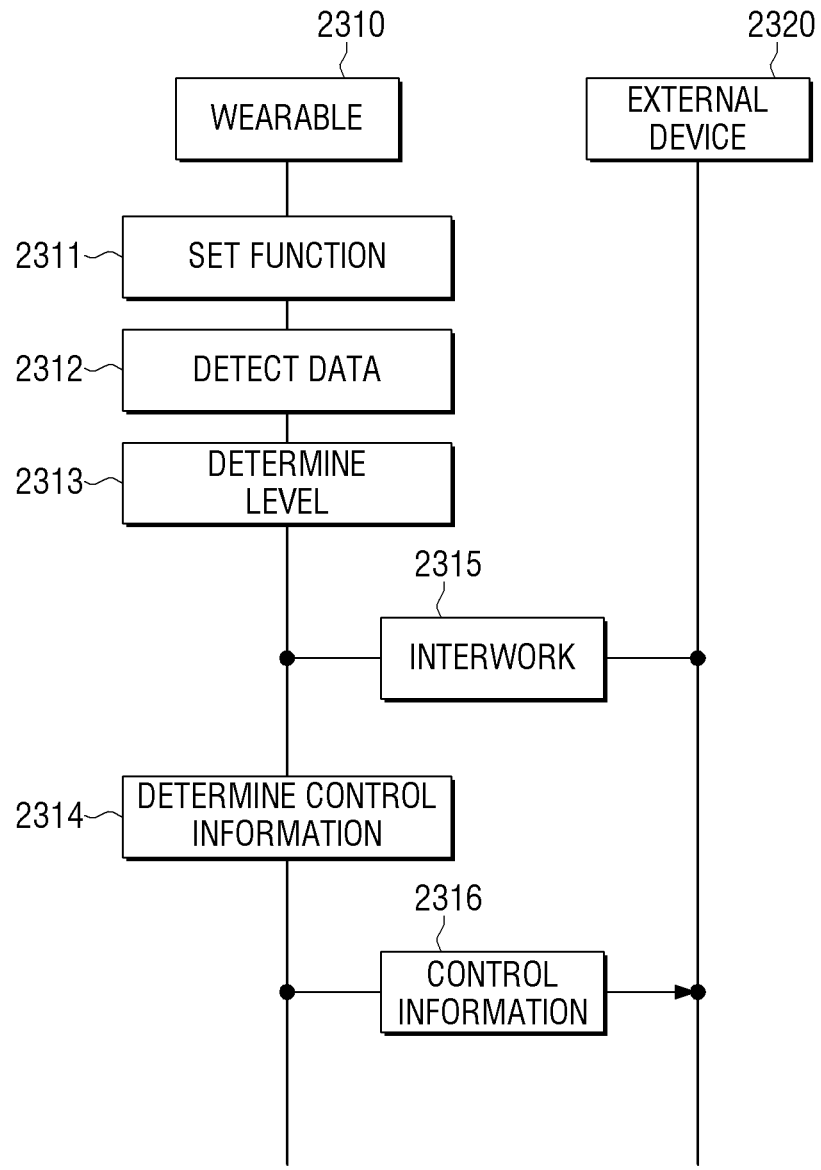
FIGS. 19 through 22 are timing charts to illustrate an operation process according to various exemplary embodiments.

Referring to FIG. 19, a timing chart of a behavior improvement system including only a wearable device 2310 and an external device 2320 is illustrated. The wearable device 2310 may set functions such as a behavior improvement item and a data detecting time according to user's manipulation at step 2311, detect data according to the set item and the set measuring time (2312), and determine a user's behavior evaluation level based on the detected data at step 2313.

In addition, the wearable device 2310 and the external device 2320 may perform an interworking process at step 2315 of establishing a communication session by performing pairing. The wearable device 2310 and the external device 2320 may perform the interworking process at step 2315 of establishing the communication session by performing pairing through communication methods such as WiFi Direct, Bluetooth, and the like.

Thereafter, in response to the interworking process at step 2315 having been completed, the wearable device 2310 may generate control information corresponding to the determined behavior evaluation level and the paired external device 2320.

In addition, the wearable device 2310 may transmit the control information to the external device 2320 at step 2316. In addition, the external device 2320 may operate according to the received control information.

Figure 20:
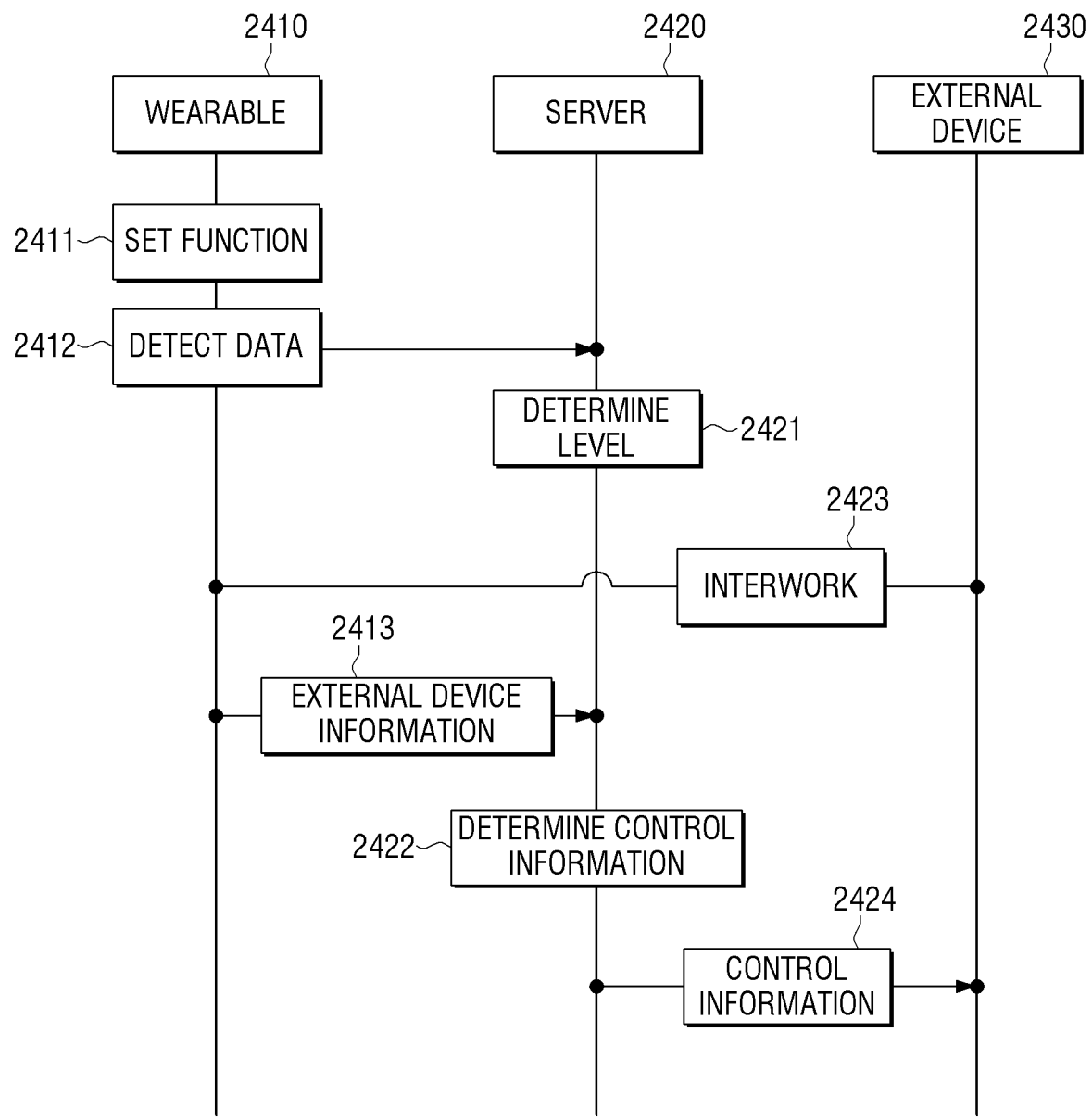

Referring to FIG. 20, a timing chart of a behavior improvement system including a wearable device 2410, a server 2420, and a second electronic device 2430 is illustrated. The wearable device 2410 may set functions such as a behavior improvement item and a data detecting time according to user's manipulation at step 2411, and detect data according to the set item and the set measuring time at step 2412. Thereafter, the wearable device 2410 may establish a communication session with the server 2420 through WiFi or an AP, and transmit the detected data to the server 2420, and the server 2420 may determine a user's behavior evaluation level based on the received data at step 2421.

In addition, the wearable device 2410 and the external device 2430 may perform an interworking process at step 2423 of establishing a communication session by performing pairing with each other. Likewise, the wearable device 2410 and the external device 2430 may perform the interworking process at step 2423 of establishing the communication session with the second electronic device 2430 through as WiFi or AP.

Thereafter, in response to the interworking process at step 2423 having been completed, the wearable device 2410 may transmit information on the paired external device 2430 to the server 2420 at step 2413.

In addition, the server 2420 may determine control information corresponding to the determined behavior evaluation level and the information on the external device 2430 received from the wearable device 2410 at step 2422.

In addition, the server 2420 may transmit the control information to the external device 2430 at step 2424.

In addition, the external device 2430 may operate according to the received control information.

Figure 21:
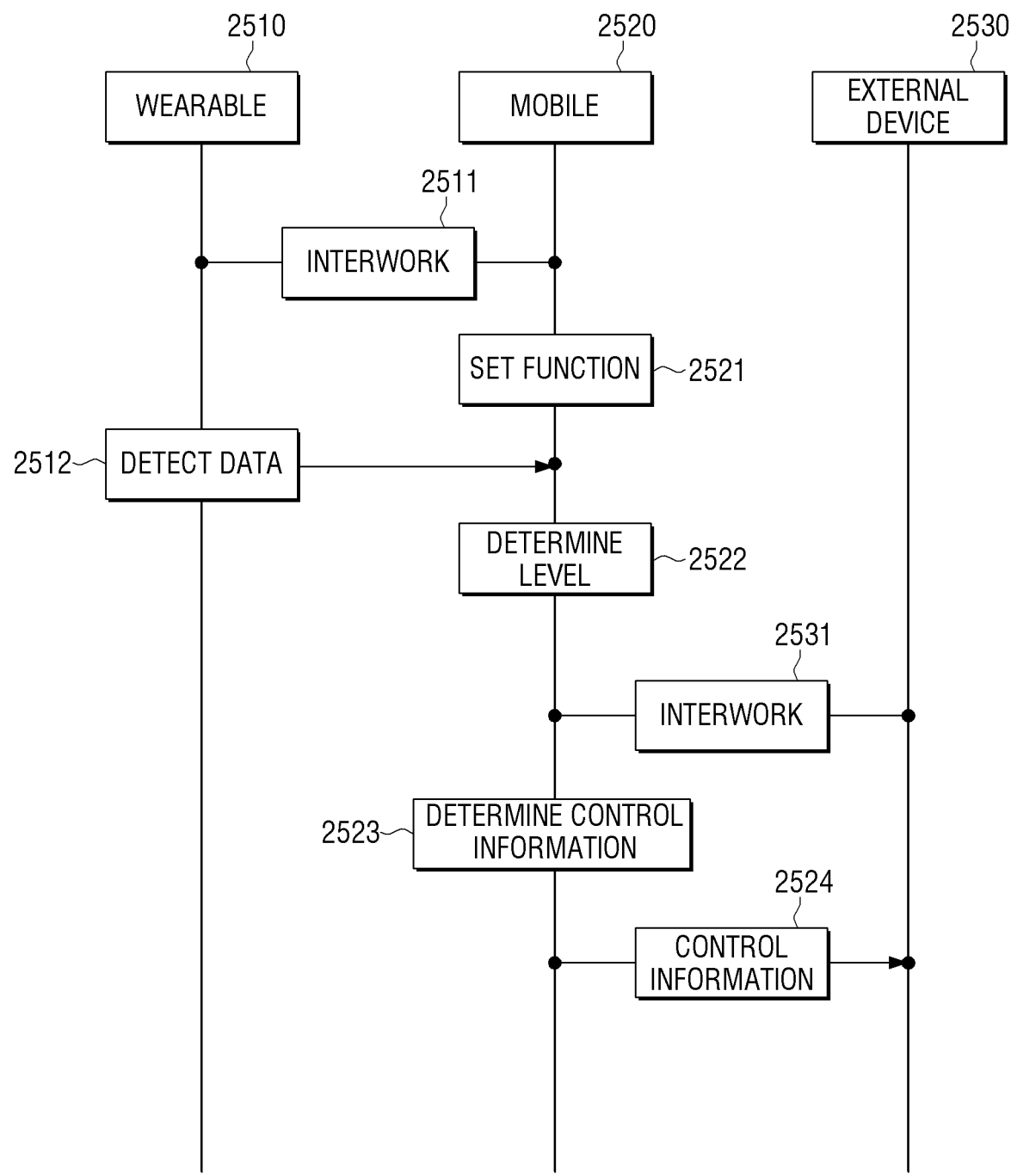

Referring to FIG. 21, a timing chart of a behavior improvement system including a wearable device 2510, a mobile device 2520, and an external device 2530 is illustrated. The wearable device 2510 and the mobile device 2520 may perform an interworking process at step 2511 of establishing a communication session by performing pairing through WiFi, WiFi Direct, and/or Bluetooth.

In response to the interworking process at step 2511 having been performed between the wearable device 2510 and the mobile device 2520, the mobile device 2520 may set functions such as a behavior improvement item and a data detecting time according to user's manipulation at step 2521, and transmit information on the set functions to the wearable device 2510, and the wearable device 2510 may detect data according to the set item and the set measuring time at step 2512. The mobile device 2520 may also detect the data according to the set item and the set measuring time. In addition, in response to the wearable device 2510 transmitting the detected data to the mobile device 2520, the mobile device 2520 may determine a user's behavior evaluation level based on the received data (2522).

In addition, the external device 2530 and the mobile device 2520 may perform an interworking process at step 2531 of establishing a communication session by performing pairing through WiFi, WiFi Direct, and/or Bluetooth.

Thereafter, in response to the interworking process at step 2531 having been completed, the mobile device 2520 may determine control information corresponding to the determined behavior evaluation level and the paired external device 2530 at step 2523.

In addition, the mobile device 2520 may transmit the control information to the external device 2530 at step 2524.

In addition, the external device 2530 may operate according to the received control information.

Figure 22:
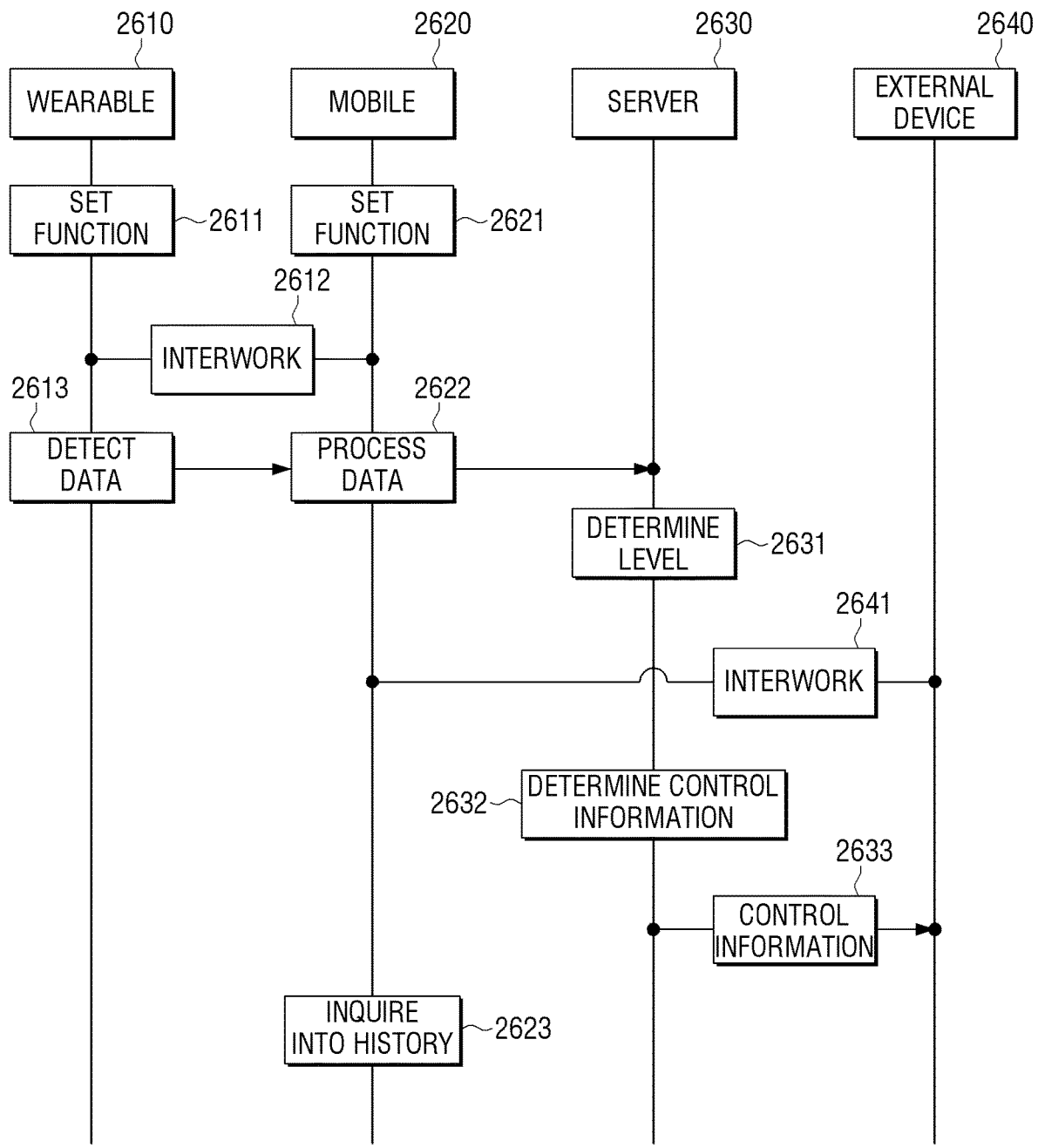

Referring to FIG. 22, a timing chart of a behavior improvement system including a wearable device 2610, a mobile device 2620, a server 2630, and an external device 2640 is illustrated. The wearable device 2610 may set functions such as a behavior improvement item and a data detecting time according to user's manipulation at step 2611. In addition, the mobile device 2620 may also set the functions such as a behavior improvement item and a data detecting time according to user's manipulation at step 2621. Thereafter, the wearable device 2610 and the mobile device 2620 may perform an interworking process at step 2612 of establishing a communication session by performing pairing through WiFi, WiFi Direct, and Bluetooth. In addition, the wearable device 2610 may detect data according to the set item and the set measuring time at step 2613. Thereafter, the wearable device 2610 may transmit the detected data to the mobile device 2620, and the mobile device 2620 may process the data received at step 2622. In addition, the mobile device 2620 may transmit the processed data to the server 2630, and the server 2630 may determine a user's behavior evaluation level based on the received data at step 2631.

In addition, the mobile device 2620 and the external device 2640 may perform an interworking process at step 2641 of establishing a communication session by performing pairing through WiFi or an AP.

Thereafter, in response to the interworking process at step 2641 having been completed, the server 2630 may determine control information corresponding to the determined behavior evaluation level and the paired external device 2640 at step 2632.

In addition, the server 2630 may transmit the control information to the external device 2640 at step 2633. Specifically, the server 2630 may receive a network address or a MAC address on the external device 2640 from the mobile device 2620, and transmit the control information to the external device 2640. In response to a request for the control information having been received from the external device 2640, the server 2630 may transmit the determined control information to the external device 2640.

In addition, the external device 2640 may operate according to the received control information.

The mobile device 2620 may store history information on the item and the measuring time which are set according to user's manipulation, and the processing of the detected data, and may inquire into the stored history information according to user's manipulation at step 2623.

In addition, as described above, the methods illustrated in FIGS. 19 through 22 may not include the process of performing user authentication with respect to the external device. However, the process of performing user authentication with respect to the external device may be included in the methods of FIGS. 19 through 22. Specifically, the user authentication for the external device may be performed before the external device performs the interworking process of establishing the communication session with at least one of the wearable device, the mobile device, and the server, or may be performed after the interworking process. The external device may perform user authentication through fingerprint recognition, face recognition, password input, and the like.

The control method of the first electronic device according to various exemplary embodiments described above may be implemented as a computer-executable program code and stored in various non-transitory computer readable media, and may be provided to respective devices to be executed by the controller.

For example, a non-transitory computer readable medium which stores a program for performing the control method, including: acquiring biological signals of a user; determining a behavior evaluation level of the user based on the biological signals; performing pairing with an external electronic device; generating control information corresponding to the determined behavior evaluation level and the paired external electronic device; and transmitting the determined control information to the paired external electronic device, may be provided.

The non-transitory computer readable medium refers to a medium that stores data semi-permanently rather than storing data for a very short time, such as a register, a cache, a memory or the like, and is readable by an apparatus. Specifically, the above-described various applications or programs may be stored in the non-transitory computer readable medium such as a compact disc (CD), a digital versatile disk (DVD), a hard disk, a Blu-ray disk, a universal serial bus (USB), a memory card, a ROM or the like, and may be provided In the above-described block diagrams showing the first electronic device, a bus is not illustrated. However, communication between the elements in the first electronic device may be performed through a bus. In addition, each of the devices may further include a controller for performing the above-described various operations, such as a CPU, a micro controller, and the like.

The foregoing exemplary embodiments and advantages are merely exemplary and are not to be construed as limiting the present disclosure. The present teaching can be readily applied to other types of apparatuses. Also, the description of the exemplary embodiments of the present disclosure is intended to be illustrative, and not to limit the scope of the claims, and many alternatives, modifications, and variations will be apparent to those skilled in the art.

What is claimed is:

1. A control method of an electronic device which controls an external electronic device, the control method comprising:
   obtaining at least one biological signal of a user;
   identifying at least one behavior of the user and a degree of the at least one behavior based on the obtained at least one biological signal;
   identifying a behavior evaluation level of the user based on the identified at least one behavior of the user and the identified degree of the at least one behavior;
   identifying at least one content executable by the user from among a plurality of contents executable in the external apparatus based on the identified behavior evaluation level of the user;
   changing environment setting of the external electronic apparatus by transmitting a command for setting the identified at least one content as a content executable by the user among the plurality of contents to the external electronic device.

2. The control method of claim 1, wherein the control information comprises at least one of available time information, available content information, and a control command regarding the paired external electronic device.

3. The control method of claim 2, wherein the available time information, the available content information, and the control command are variable according to the behavior evaluation level identified.

4. The control method of claim 1, wherein the behavior evaluation level is identified based on a value which is calculated by digitizing the plurality of biological signals acquired by weighting at least one item of activity, linguistic behavior, and impulsivity.

5. The control method of claim 1, wherein transmitting the control information comprises transmitting the control information to the external electronic device in response to the user of the electronic device performing user authentication with respect to the paired external electronic device.

6. The control method of claim 1, further comprising providing feedback according to the behavior evaluation level identified.

7. The control method of claim 1, further comprising receiving an input of user manipulation to set a behavior improvement item of the user and a behavior pattern measuring time, and
wherein acquiring at least one biological signal comprises identifying a behavior pattern related to the behavior improvement item, and detecting data for measuring the behavior pattern identified according to the behavior pattern measuring time.

8. The control method of claim 1, wherein identifying the behavior evaluation level comprises:
grouping user's behavior patterns which are measured based on the at least one biological signal to a plurality of predetermined items;
calculating an average by weighting the grouped user's behavior patterns according to each of the plurality of predetermined items, and
identifying the behavior evaluation level based on the average calculated.

9. The control method of claim 8, wherein the identifying the behavior evaluation level comprises comparing the average calculated and a predetermined reference value and identifying the behavior evaluation level according to a deviation.

10. The control method of claim 1, further comprising storing behavior pattern history information of the user, and
wherein the identifying the behavior evaluation level comprises measuring a similarity between behavior pattern of the user which is measured based on the at least one biological signal, and the behavior pattern history information of the user, and identifying the behavior evaluation level.

11. The control method of claim 1, further comprising transmitting, to the paired external electronic device, a control signal for displaying an image on the user through the paired external electronic device according to the behavior evaluation level identified.

12. An electronic device for controlling an external electronic device, the electronic device comprising:
a sensor;
a communicator comprising communication circuitry; and
a controller configured to:
obtain at least one biological signal of a user through the sensor,
identify at least one behavior of the user and a degree of the at least one behavior based on the obtained at least one biological signal,
identify a behavior evaluation level of the user based on the identified at least one behavior of the user and the identified degree of the at least one behavior, and
identify at least one content executable by the user from among a plurality of contents executable in the external apparatus based on the identified behavior evaluation level of the user,
change environment setting of the external electronic apparatus by transmitting, through the communicator, a command for setting the identified at least one content as a content executable by the user among the plurality of contents to the external electronic device.

13. The electronic device of claim 12, wherein the control information comprises at least one of available time information, available content information, and a control command regarding the paired external electronic device.

14. The electronic device of claim 13, wherein the control command comprises information for controlling the paired external electronic device to operate based on at least one of the available time information and the available content information.

15. The electronic device of claim 12, wherein the behavior evaluation level is identified based on a value which is calculated by digitizing the at least one biological signal acquired by weighting at least one item of activity, linguistic behavior, and impulsivity.

16. The electronic device of claim 13, wherein the available time information, the available content information, and the control command are variable according to the behavior evaluation level identified.

17. The electronic device of claim 12, wherein the controller is configured to transmit the control information to the external electronic device in response to the user of the electronic device performing user authentication with respect to the paired external electronic device.

18. The electronic device of claim 12, wherein the controller is configured to provide feedback according to the behavior evaluation level identified.

19. The electronic device of claim 12, further comprising an input configured to receive an input of user manipulation to set a behavior improvement item of the user and a behavior pattern measuring time, and
wherein the controller is configured to identify a behavior pattern related to the behavior improvement item, and control the sensor to detect data for measuring the behavior pattern identified according to the behavior pattern measuring time.

20. A server comprising:
a communicator configured to communicate with a first electronic device and a second electronic device; and
a controller configured to:
receive, through the communicator, at least one biological signal of a user from the first electronic device,
identify at least one behavior of the user and a degree of the at least one behavior based on the received at least one biological signal,
identify a behavior evaluation level of the user based on the identified at least one behavior of the user and the identified degree of the at least one behavior, and
identify at least one content executable by the user from among a plurality of contents executable in the second electronic device based on the identified behavior evaluation level of the user,
change environment setting of the second electronic device by transmitting, through the communicator, a command for setting the identified at least one content as a content executable by the user among the plurality of contents to the second electronic device.

* * * * *